(12) United States Patent
Nakamura et al.

(10) Patent No.: US 8,569,538 B2
(45) Date of Patent: Oct. 29, 2013

(54) ACRYLOYL MATERIALS FOR MOLDED PLASTICS

(75) Inventors: Masataka Nakamura, Shiga (JP); Mitsuru Yokota, Shiga (JP); Takehiro Kohara, Shiga (JP); Kimihiro Kamasaka, Hyogo (JP); Hiroya Koyama, Shimane (JP); Shinya Kiguchi, Hyogo (JP); Satoshi Umeda, Shimane (JP)

(73) Assignees: Johnson & Johnson Vision Care, Inc., Jacksonville, FL (US); Toray Industries, Inc., Tokyo (JP)

( * ) Notice: Subject to any disclaimer, the term of this patent is extended or adjusted under 35 U.S.C. 154(b) by 249 days.

(21) Appl. No.: 11/609,724

(22) Filed: Dec. 12, 2006

(65) Prior Publication Data

US 2008/0004383 A1    Jan. 3, 2008

Related U.S. Application Data

(60) Provisional application No. 60/818,016, filed on Jun. 30, 2006.

(51) Int. Cl.
*C07C 69/00* (2006.01)
(52) U.S. Cl.
USPC .......................................................... 560/129
(58) Field of Classification Search
None
See application file for complete search history.

(56) References Cited

U.S. PATENT DOCUMENTS

| | | | |
|---|---|---|---|
| 2,793,223 A * | 5/1957 | Merker | 556/440 |
| 2,956,044 A * | 10/1960 | Merker | 526/279 |
| 3,001,975 A | 9/1961 | Beavers et al. | 526/279 |
| 3,057,902 A * | 10/1962 | Pike | 556/479 |
| 3,563,742 A * | 2/1971 | Phlipot | 430/254 |
| 3,699,081 A | 10/1972 | Iwashita et al. | 564/4 |
| T908,001 I4 | 3/1973 | Besser | 560/4 |
| 3,756,820 A | 9/1973 | Hayakawa et al. | |
| 3,859,320 A * | 1/1975 | Atherton | 556/422 |
| 3,865,588 A | 2/1975 | Ohto et al. | |
| 3,959,358 A | 5/1976 | Jursich | |
| 4,117,001 A | 9/1978 | Fozzard | |
| 4,120,570 A | 10/1978 | Gaylord | 351/40 |
| 4,139,513 A | 2/1979 | Tanaka et al. | |
| 4,139,692 A | 2/1979 | Tanaka et al. | 526/218 |
| 4,144,137 A | 3/1979 | Stewart | 203/65 |
| 4,235,985 A | 11/1980 | Tanaka et al. | 526/279 |
| 4,259,467 A | 3/1981 | Keogh et al. | 526/279 |
| 4,260,725 A | 4/1981 | Keogh et al. | 526/279 |
| 4,395,496 A * | 7/1983 | Wittmann et al. | 523/107 |
| 4,402,887 A | 9/1983 | Kuriyama et al. | |
| 4,463,149 A | 7/1984 | Ellis | |
| 4,563,538 A | 1/1986 | Wakabayashi et al. | |
| 4,602,074 A | 7/1986 | Mizutani et al. | |
| 4,632,968 A | 12/1986 | Yokota et al. | 526/279 |

(Continued)

FOREIGN PATENT DOCUMENTS

| BR | 7403534 | 4/1974 |
|---|---|---|
| CN | 200780043363.1 | 9/2007 |

(Continued)

OTHER PUBLICATIONS

International Search Report and Written Opinion for PCT/US2007/015264 filed Jun. 28, 2007.

(Continued)

*Primary Examiner* — Johann R Richter
*Assistant Examiner* — Jennifer C Sawyer
(74) *Attorney, Agent, or Firm* — Ballard Spahr LLP

(57) ABSTRACT

In one aspect, the invention relates to methods of synthesizing acryloyl compounds, comprising the step of hydrosilylating a compound having the structure:

with a compound having the structure A-H, wherein A comprises a siloxanyl group, to yield a compound having the structure:

Compounds and compositions produced thereby can effectively attain a satisfactory balance between high oxygen permeability and hydrophilicity while achieving an acceptably low concentration of undesirable impurities. This abstract is intended as a scanning tool for purposes of searching in the particular art and is not intended to be limiting of the present invention.

6 Claims, 2 Drawing Sheets

(56) References Cited

U.S. PATENT DOCUMENTS

| | | | |
|---|---|---|---|
| 4,853,453 A | 8/1989 | Schafer et al. | 528/28 |
| 4,861,850 A * | 8/1989 | Novicky | 526/243 |
| 5,010,141 A | 4/1991 | Mueller | 525/276 |
| 5,045,233 A | 9/1991 | Kita et al. | |
| 5,045,621 A | 9/1991 | Suzuki | |
| 5,057,578 A | 10/1991 | Spinelli | 525/278 |
| 5,079,319 A | 1/1992 | Mueller | 526/238.23 |
| 5,128,484 A | 7/1992 | Kita et al. | |
| 5,219,965 A | 6/1993 | Valint, Jr. et al. | 526/245 |
| 5,244,981 A | 9/1993 | Seidner et al. | |
| 5,314,960 A | 5/1994 | Spinelli et al. | 525/280 |
| 5,321,108 A | 6/1994 | Kunzler et al. | 526/242 |
| 5,329,034 A | 7/1994 | Nagase et al. | |
| 5,336,797 A | 8/1994 | McGee et al. | 556/419 |
| 5,356,947 A | 10/1994 | Ali et al. | |
| 5,371,147 A | 12/1994 | Spinelli et al. | 525/288 |
| 5,387,662 A | 2/1995 | Kunzler et al. | 526/245 |
| 5,387,663 A | 2/1995 | McGee et al. | 526/279 |
| 5,470,930 A | 11/1995 | Toba et al. | 526/204 |
| 5,481,015 A * | 1/1996 | Nomura | 556/405 |
| 5,493,039 A | 2/1996 | Okawa et al. | |
| 5,510,428 A | 4/1996 | Harano et al. | 525/438 |
| 5,539,016 A | 7/1996 | Kunzler et al. | 523/107 |
| 5,554,706 A | 9/1996 | Nagase et al. | |
| 5,563,184 A | 10/1996 | McGee et al. | 523/107 |
| 5,610,252 A | 3/1997 | Bambury et al. | 526/279 |
| 5,831,110 A | 11/1998 | Isoda et al. | |
| 5,888,356 A | 3/1999 | Keil et al. | |
| 5,891,977 A * | 4/1999 | Dietz et al. | 528/15 |
| 5,959,117 A | 9/1999 | Ozark et al. | |
| 5,962,548 A | 10/1999 | Vanderlaan et al. | |
| 5,994,488 A | 11/1999 | Yokota et al. | |
| 6,031,059 A | 2/2000 | Vanderlaan et al. | |
| 6,177,585 B1 | 1/2001 | Chen et al. | 556/479 |
| 6,180,741 B1 | 1/2001 | Yamaguchi et al. | 526/301 |
| 6,218,503 B1 | 4/2001 | Lai et al. | 528/320 |
| 6,242,153 B1 | 6/2001 | Sato et al. | |
| 6,306,992 B1 * | 10/2001 | Yoshitake et al. | 526/279 |
| 6,334,935 B1 | 1/2002 | Uehara et al. | 203/8 |
| 6,344,495 B1 | 2/2002 | Ueda et al. | |
| 6,350,816 B1 | 2/2002 | Farronato et al. | |
| 6,372,815 B1 | 4/2002 | Sule et al. | 523/106 |
| 6,617,373 B2 | 9/2003 | Sule et al. | 523/108 |
| 6,649,722 B2 | 11/2003 | Rosenzwig et al. | |
| 6,783,897 B2 * | 8/2004 | Kang et al. | 429/313 |
| 6,787,615 B2 * | 9/2004 | Keller et al. | 525/477 |
| 6,803,406 B2 | 10/2004 | Musa | |
| 6,809,155 B2 | 10/2004 | Musa | |
| 6,822,016 B2 | 11/2004 | McCabe et al. | |
| 6,846,892 B2 | 1/2005 | Kindt-Larsen et al. | 526/320 |
| 6,908,969 B2 | 6/2005 | Musa | |
| 6,922,118 B2 | 7/2005 | Kubena et al. | 333/188 |
| 6,933,401 B2 * | 8/2005 | Molock et al. | 556/437 |
| 7,169,874 B2 | 1/2007 | Salamone et al. | |
| RE39,635 E | 5/2007 | Vanderlaan et al. | |
| 7,317,117 B2 * | 1/2008 | Nakamura et al. | 556/443 |
| 7,368,589 B2 | 5/2008 | Mahadevan et al. | |
| 7,461,937 B2 | 12/2008 | Steffan et al. | |
| 7,838,698 B2 | 11/2010 | Fujisawa et al. | |
| 2002/0016383 A1 | 2/2002 | Iwata et al. | 523/106 |
| 2003/0109661 A1 | 6/2003 | Salamone et al. | 528/25 |
| 2003/0125498 A1 | 7/2003 | McCabe et al. | |
| 2003/0130465 A1 | 7/2003 | Lai et al. | 528/25 |
| 2003/0203986 A1 | 10/2003 | Valet | |
| 2004/0014921 A1 | 1/2004 | Fujisawa et al. | |
| 2004/0106694 A1 | 6/2004 | Fujisawa et al. | |
| 2004/0114101 A1 | 6/2004 | Thakrar | |
| 2004/0198916 A1 | 10/2004 | Nakamura et al. | |
| 2004/0198938 A1 | 10/2004 | Nakamura et al. | |
| 2004/0201820 A1 | 10/2004 | Nakamura et al. | |
| 2004/0249180 A1 * | 12/2004 | Nakamura et al. | 556/443 |
| 2005/0165246 A1 | 7/2005 | Lai et al. | 556/413 |
| 2005/0237483 A1 | 10/2005 | Phelan | |
| 2006/0007391 A1 | 1/2006 | McCabe et al. | |
| 2006/0036052 A1 | 2/2006 | Kindt-Larsen et al. | 526/320 |
| 2006/0047134 A1 | 3/2006 | Molock et al. | |
| 2006/0223964 A1 | 10/2006 | Lai et al. | 528/32 |
| 2006/0229423 A1 * | 10/2006 | Parakka et al. | 528/37 |
| 2007/0203275 A1 * | 8/2007 | Kikuchi et al. | 524/266 |
| 2008/0004383 A1 * | 1/2008 | Nakamura et al. | 524/284 |
| 2008/0004401 A1 | 1/2008 | Nakamura et al. | |
| 2008/0081850 A1 | 4/2008 | Fujisawa et al. | |
| 2008/0081894 A1 | 4/2008 | Fujisawa et al. | |
| 2008/0119627 A1 | 5/2008 | Nakamura et al. | |
| 2008/0143003 A1 | 6/2008 | Phelan | |
| 2009/0156708 A1 | 6/2009 | Lai et al. | 523/107 |
| 2011/0028673 A1 | 2/2011 | Fujisawa et al. | |

FOREIGN PATENT DOCUMENTS

| | | | |
|---|---|---|---|
| CN | 200780044049.5 | 9/2007 | |
| EP | 0306756 A2 | 3/1989 | |
| EP | 0 639 576 | 2/1995 | |
| EP | 0 733 637 | 9/1996 | |
| EP | 0 753 521 | 1/1997 | |
| EP | 0 965 593 | 12/1999 | |
| EP | 1 123 915 | 8/2001 | |
| EP | 1 386 924 | 2/2004 | |
| EP | 1 403 396 | 3/2004 | |
| EP | 1 426 809 A1 | 6/2004 | |
| EP | 1 719 776 | 11/2006 | |
| EP | 1 749 812 | 2/2007 | |
| EP | 07 874 059.4 | 6/2007 | |
| EP | 07 838 814.7 | 9/2007 | |
| EP | 07838800.6 | 9/2007 | |
| GB | 1 364 360 | 8/1974 | |
| JP | 50-014786 | 2/1975 | |
| JP | 52-168545 | 12/1977 | |
| JP | 55-015110 | 2/1980 | |
| JP | 56-022325 | 3/1981 | |
| JP | 63-301919 | 8/1988 | |
| JP | 63-216044 | 9/1988 | |
| JP | 63216044 | 9/1988 | |
| JP | 04-077489 | 3/1992 | |
| JP | 06-032791 | 2/1994 | |
| JP | 08-283342 | 10/1996 | |
| JP | 2000191667 A * | 7/2000 | C07F 7/08 |
| JP | 2000191730 A * | 7/2000 | C08F 30/08 |
| JP | 2001048939 * | 2/2001 | |
| JP | 2004115790 | 4/2004 | |
| JP | 2006036757 | 2/2006 | |
| WO | WO/96/31792 | 10/1996 | |
| WO | WO/01/71392 | 9/2001 | |
| WO | WO/02/081532 | 10/2002 | |
| WO | WO 03/014130 | 2/2003 | |
| WO | WO 03/021336 | 3/2003 | |
| WO | WO/03/022322 | 3/2003 | |
| WO | WO 03/027123 | 4/2003 | |
| WO | WO/03/040193 | 5/2003 | |
| WO | WO/03/043668 | 5/2003 | |
| WO | WO/03/066688 | 8/2003 | |
| WO | WO/03/077792 | 9/2003 | |
| WO | WO/2005/115958 | 5/2004 | |
| WO | WO 2005/005368 | 1/2005 | |
| WO | WO 2005/005445 | 1/2005 | |
| WO | WO 2005/044829 | 5/2005 | |
| WO | WO/2005/090364 | 9/2005 | |
| WO | WO 2008/005398 | 1/2008 | |
| WO | WO/2008/005398 | 1/2008 | |

OTHER PUBLICATIONS

Künzler, "Silicone Hydrogels for Contact Lens Application," *Trends in Polymer Science*, 4(2):52-59 (1996).

Lai, "Role of Bulky Polysiloxanylalkyl Methacrylates in Oxygen-Permeable Hydrogel Materials," *Journal of Applied Polymer Science*, 56(3):317-324 (1995).

Adams, et al., "Metal Segregation in Bimetallic Clusters and Its Possible Role in Synergism and Bifunctional Catalysis," 2000, Journal of Organometallic Chemistry, vol. 600, p. 1-6.

International Search Report for International Application No. PCT/US2007/015264 (mailed May 12, 2007).

International Search Report for International Application No. PCT/US2007/020668 (mailed Jan. 25, 2008).

(56) References Cited

OTHER PUBLICATIONS

International Search Report for International Application No. PCT/US2007/020683 (mailed Jan. 25, 2008).
International Search Report for International Application No. PCT/US2007/024325 (mailed Apr. 24, 2008).
Hirabayashi et al., "A facile preparation and cyclopropanation of 1-alkenylsilanols," Bulletin of the Chemical Society of Japan, 71(10):2409-2417 (1998).
HQMME Product Literature, Eastman Chemicals website (2008).
Kawakami et al., "Synthesis and characterization of liquid crystalline polystyrenes with disiloxane linkage in the spacer," *Polymer Bulletin (Berlin)*, 36(6):653-658 (1996).
Plueddemann et al., "Epoxyorganosilozanes," *J. Am. Chem Soc.*, 81:2632-2635 (1959).
Volkova et al., "Reaction of dimethylsiloxacyclohexane with methacrylic acid and triethylsilanol: Synthesis of [(mehtacryloyloxy)butyl]dimethyl(triethylsiloxy)silane," *Zhurnal Obshchei Khimii*, 58(9):2145-2148 (1988).
Fortuniak, "Controlled Synthesis of Siloxan Polymers and Siloxan-Siloxane Block Copolymers with 3-Chloropropyl Groups Pendat to the Siloxane Chain," Macromol. Chem. Phys. 2001, 202, 2306-2313.
Gaylord, "Composition for Manufacturing Contact Lenses," Accession No. 1976:578430, based on Brazilian Patent No. 7403534.
Material Safety Data Sheet of 2-Ethylhexyl acrylate, Japan Petrochemical Industry Association, May 25, 1986 (revised in Aug. 2001), p. 4-5, Item 10, 11.1-10, available at http://www.jpca.or.jp/61msds/j7cb32.htm (accessed Jul. 17, 2008).
Supplemental Notice of Allowance issued on Oct. 6, 2011 for U.S. Appl. No. 11/609,677, filed Dec. 12, 2006 (Inventor—Nakamura et al.; pp. 1-5).
Response to Restriction Requirement filed on Oct. 27, 2011 for U.S. Appl. No. 12/901,191, filed Oct. 8, 2010 (Inventor—Fujisawa et al.; pp. 1-16).
Non-Final Office Action issued on Dec. 20, 2011 for U.S. Appl. No. 12/901,191, filed Oct. 8, 2010 (Inventor—Fujisawa et al.; pp. 1-5).
Final Office Action issued on Sep. 29, 2011 for U.S. Appl. No. 11/561,525, filed Nov. 20, 2006 (Inventor—Fujisawa et al.; pp. 1-10).
Supplemental Notice of Allowance issued on Oct. 13, 2011 for U.S. Appl. No. 11/771,999, filed Jun. 29, 2007 (Inventor—Fujisawa et al.; pp. 1-5).
Response to Office Action filed on Nov. 17, 2011 for CN Pat. App. No. 200780044049.5, national phase of PCT/US2007/020683 filed Sep. 25, 2007 (Inventor—Fujisawa et al.; Applicant—Johnson & Johnson Vision Care, Inc.; pp. 1-27).
Response to Office Action filed on Nov. 18, 2011 for CN Pat. App. No. 200780043363.1, national phase of PCT/US2007/020668 filed Sep. 25, 2007 (Inventor—Fujisawa et al.; Applicant—Johnson & Johnson Vision Care, Inc.; pp. 1-19).
Hurd, On the Mechanism of the Acid-catalyzed Rearrangement of Siloxane Linkages in Organopolysiloxanes, Journal of the American Chemical Society, Jun. 1955, vol. 77, pp. 2998-3001.
Response to Office Communication filed on Feb. 6, 2012 for EP Pat. App. No. 07874059.4, national phase of Intl. Pat. App. No. PCT/US2007/015150 filed Jun. 28, 2007 (Inventor—Nakamura; Applicant—Johnson & Johnson Vision Care, Inc.; pp. 1-9).
Second Office Action issued on Dec. 6, 2011 for CN Pat. App. No. 200780043363.1, national phase of PCT/US2007/020668 filed Sep. 25, 2007 (Inventor—Fujisawa et al.; Applicant—Johnson & Johnson Vision Care, Inc.; pp. 1-16).
Response to Office Action filed on Mar. 28, 2012 for U.S. Appl. No. 11/561,525, filed Nov. 20, 2006 (Inventor—Fujisawa et al.; pp. 1-13).
Non-Final Office Action issued on Mar. 5, 2012 for U.S. Appl. No. 13/300,576, filed Nov. 19, 2011 (Inventor—Fujisawa et al.; pp. 1-8).
U.S. Appl. No. 11/609,677, filed Dec. 12, 2006, Nakamura, Response to the Rejection mailed by the PTO on May 11, 2009.
U.S. Appl. No. 11/561,456, filed Nov. 20, 2006, Fujisawa, Non-Final Rejection mailed by the PTO on Oct. 27, 2009.
U.S. Appl. No. 11/681,406, filed Mar. 2, 2007, Nakamura, Response to the Final Rejection mailed by the PTO on Jul. 6, 2009.
U.S. Appl. No. 11/609,677, filed Dec. 12, 2006, Nakamura, Office Action mailed Nov. 9, 2010.
U.S. Appl. No. 11/561,525, filed Nov. 20, 2006, Fujisawa, Response to final Office Action mailed May 24, 2010.
U.S. Appl. No. 11/771,999, filed Jun. 29, 2007, Fujisawa, Office Action mailed Oct. 15, 2010.
U.S. Appl. No. 12/060,536, filed Apr. 1, 2008, Fujisawa, Response to Office Action mailed Mar. 18, 2010.
U.S. Appl. No. 12/060,536, filed Apr. 1, 2008, Fujisawa, Notice of Allowance mailed Oct. 19, 2010.
U.S. Appl. No. 11/561,525, filed Nov. 20, 2006, Fujisawa, Office Action mailed Jan. 4, 2011.
U.S. Appl. No. 11/771,999, filed Jun. 29, 2007, Fujisawa, Response to Office Action mailed Oct. 15, 2010.
U.S. Appl. No. 11/609,677, filed Dec. 12, 2006, Nakamura, Response to Office Action mailed Nov. 9, 2010.
U.S. Appl. No. 12/901,191, filed Oct. 8, 2010, Fujiswa, Office Action mailed Apr. 27, 2011.
U.S. Appl. No. 11/771,999, filed Jun. 29, 2007, Fujisawa, Final Rejection Action mailed Apr. 1, 2011.
U.S. Appl. No. 11/609,677, filed Dec. 12, 2006, Nakamura, Notice of Allowance mailed, Jul. 21, 2011.
U.S. Appl. No. 11/561,525, filed Nov. 20, 2006, Fujisawa, Response to Office Action mailed Jan. 4, 2011.
U.S. Appl. No. 11/771,999, filed Jun. 29, 2007, Fujisawa, Response to Office Action mailed Apr. 1, 2011.
U.S. Appl. No. 11/771,999, filed Jun. 29, 2007, Fujisawa, Notice of Allowance mailed, Aug. 19, 2011.

* cited by examiner

ACRYLOYL MATERIALS FOR MOLDED PLASTICS

CROSS REFERENCE TO RELATED APPLICATIONS

This application claims the benefit of U.S. Application No. 60/818,016 filed Jun. 30, 2006, which is hereby incorporated herein by reference in its entirety.

BACKGROUND

Acryloyl-functionalized linear polydimethylsiloxanes can have a satisfactory oxygen permeability yet suffer from hydrophobicity, thereby repelling water and increasing the incidence of corneal staining. That is, introduction of a siloxanyl group for the purpose of increasing oxygen permeability can negatively impact other properties of the composition. Further, when an acryloyl-functionalized polydimethylsiloxane is copolymerized with a hydrophilic monomer (e.g., 2-hydroxyethyl(meth)acrylate) in order to increase the hydrophilicity, phase separation can occur due to the static repulsion between the polar hydroxyl group and the nonpolar siloxanyl group, so that a transparent polymer cannot be obtained. Accordingly, such compositions can have poor optical quality.

Moreover, some acryloyl-functionalized polydimethylsiloxane compositions produced by an addition reaction between an epoxy compound having a siloxanyl group and (meth)acrylic acid can contain unsatisfactory concentrations of undesirable impurities, for example, epoxide or diol moieties that can have irritating properties when the compositions are used as, for example, contact lenses and intraocular lenses.

Therefore, there remains a need for methods and compositions that overcome these deficiencies and that effectively attain a satisfactory balance between improved oxygen permeability and hydrophilicity while achieving an acceptably low concentration of undesirable impurities.

SUMMARY

As embodied and broadly described herein, the invention, in one aspect, relates to methods of synthesizing acryloyl compounds, comprising the step of hydrosilylating a first compound having the structure:

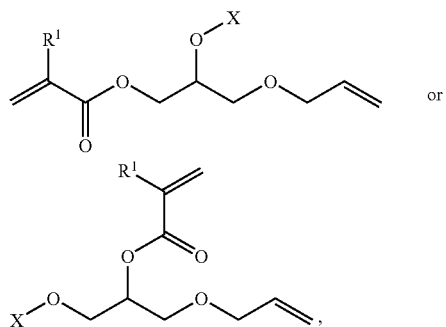

wherein $R^1$ represents hydrogen, $C_1$-$C_{18}$ alkyl, or phenyl, and wherein X represent hydrogen or a hydrolysable group; with a second compound having the structure A-H, wherein A comprises a siloxanyl group, to yield a third compound having the structure:

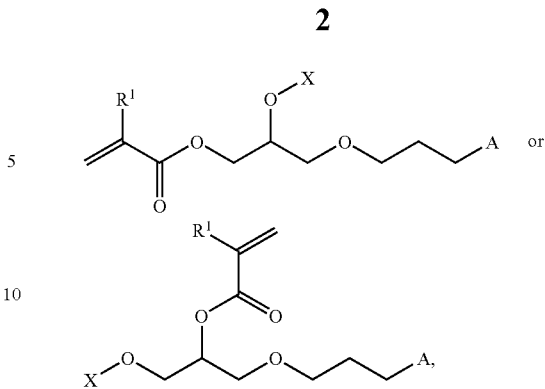

wherein X is hydrogen or a hydrolysable group; and wherein A is a siloxanyl group. Compounds and compositions produced thereby can effectively attain a satisfactory balance between oxygen permeability and hydrophilicity while achieving an acceptably low concentration of undesirable impurities.

In a yet further aspect, the invention relates to the products of the disclosed methods. For example, in one aspect, the invention relates to acryloyl compounds comprising the structure:

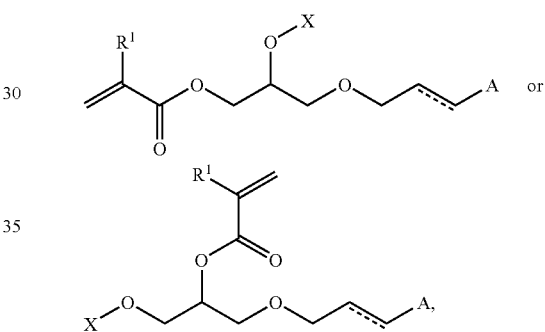

wherein $R^1$ is hydrogen, $C_1$-$C_{18}$ alkyl, or phenyl; wherein X is hydrogen or a hydrolysable group; wherein A is hydrogen and - - - is a double bond, or wherein A comprises a siloxanyl group and - - - is a single bond; and wherein X and A are not simultaneously hydrogen, as well as compositions produced therefrom.

Such compositions can be suitable for producing molded articles, can be excellent in transparency, hydrophilicity, mechanical properties, and oxygen permeability, and can have a low modulus of elasticity and/or an excellent optical quality, so as to be suitable for ophthalmic lenses such as contact lenses and intraocular lenses.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments and together with the description illustrate the disclosed compositions and methods.

DETAILED DESCRIPTION

Figure 1:
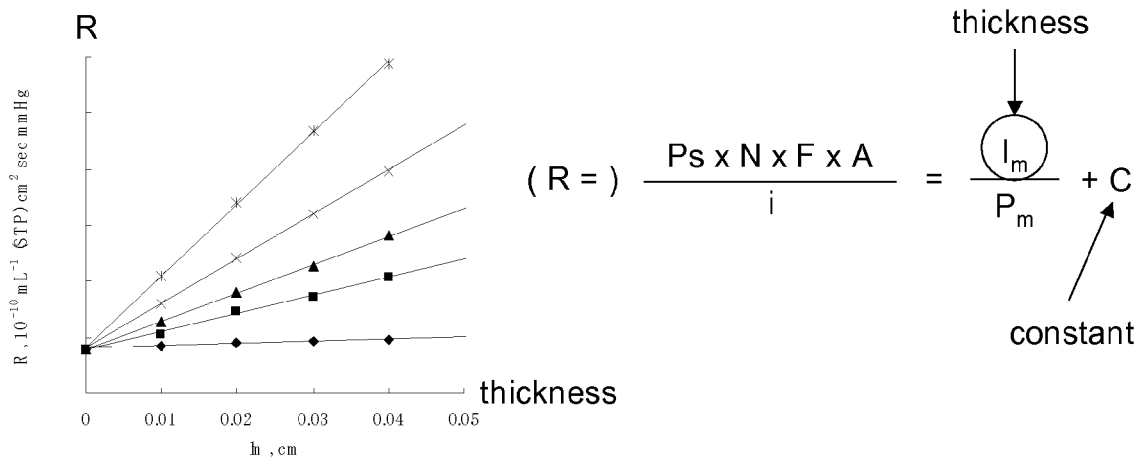
FIG. 1 shows a plot of R (1/Q) versus thickness (1 m).

The present invention can be understood more readily by reference to the following detailed description of the invention and the Examples included therein.

Before the present compounds, compositions, articles, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular embodiments only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein may be different from the actual publication dates, which may need to be independently confirmed.

A. Definitions

As used in the specification and the appended claims, the singular forms "a," "an" and "the" include plural referents unless the context clearly dictates otherwise. Thus, for example, reference to "a component," "a polymer," or "a residue" includes mixtures of two or more such components, polymers, or residues, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the terms "optional" or "optionally" means that the subsequently described event or circumstance may or may not occur, and that the description includes instances where said event or circumstance occurs and instances where it does not.

As used herein, the term "copolymer" refers to a polymer formed from two or more different repeating units (monomer residues). By way of example and without limitation, a copolymer can be an alternating copolymer, a random copolymer, a block copolymer, or a graft copolymer.

As used herein, the term "siloxanyl" refers to a structure having at least one Si—O—Si bond. Thus, for example, siloxanyl group means a group having at least one Si—O—Si group, and siloxanyl compound means a compound having at least one Si—O—Si group.

As used herein, the term "siloxanyl monomer" refers to a siloxanyl compound having at least one polymerizable carbon-carbon unsaturated bond. In one aspect, the polymerizable carbon-carbon unsaturated bond can be part of an alkylacryloyl moiety (e.g., acryloyl or a methacryloyl moiety).

As used herein, the term "alkylacrylic acid" refers to acrylic acid, alkyl-substituted acrylic acids, salts thereof, and derivatives thereof. In one aspect, an alkylacrylic acid can be further substituted. In a further aspect, an alkylacrylic acid is methacrylic acid.

As used herein, the term "hydrolyzable group" refers to a group or moiety which is convertible to hydrogen by hydrolysis or solvolysis. In one aspect, a hydrolyzable group can be hydrolyzed (i.e., converted to a hydrogen group) by exposure to water or a protic solvent at or near ambient temperature and at or near atmospheric pressure. In further aspects, a hydrolyzable group can be hydrolyzed by exposure to water or a protic solvent at an elevated temperature or an elevated pressure. In further aspects, a hydrolyzable group can be hydrolyzed by exposure to acidic or alkaline water or acidic or alkaline protic solvent. Suitable hydrolyzable groups include, without limitation, residues of dihydropyran, residues of alkyl halide, residues of tosyloxyalkane, residues of diazoalkane, residues of dialkyl sulfate, residues of an acid anhydride, residues of an acid halide, residues of a halogenated silane, and residues of a silazane.

As used herein, the term "reduced pressure distillation" refers to the act of purifying liquids through evaporating or boiling at a pressure lower than about atmospheric pressure (i.e., about 1000 mbar or about 760 Torr), so that the gaseous vapors condense to a pure liquid. Pollutants and contaminants typically remain in a concentrated residue. The pressure can be, for example, less than about 100 mbar, less than about 10 mbar, less than about 1 mbar, less than about 0.1 mbar, less than about 0.05 mbar, or less than about 0.02 mbar. An apparatus for distilling typically includes a distilling vessel (which holds the pre-distillation material during heating), a condenser (which cools the evaporated material), and a receiving vessel (which collects the distillate). In one aspect, distillation does not include chemical vapor deposition.

As used herein, the term "thin film distillation" refers to short path distillation wherein a substantial decrease of boiling temperature is obtained by reducing the operating pressure. This can allow thermal separation of products that would be destroyed by conventional vacuum distillation (pot still or distillation column) because of the necessary high temperatures and long residence time. In one aspect, this term refers to a distillation operation in which a thin layer of liquid is subjected to distillation. Therefore, the operations generally called thin film distillation, molecular distillation, short path distillation, thin film evaporation, short path evaporation, and the like, are within the scope of "thin film distillation."

As used herein, the term "polymerization inhibitor," sometimes also referred to as a "radical inhibitor" or a "radical scavenger," refers to a substance that impedes or retards the process of polymerization. Typically, such an inhibitor slows or prevents the formation of radicals, which can initiate polymerization. Alternatively, such an inhibitor can react with any formed radicals at a rate greater than the polymerization initiation and/or propagation steps. Examples of suitable polymerization inhibitors include alkylhydroquinones and hydroxynaphthalenes.

In one aspect, a polymerization inhibitor can be present during the distillation of the disclosed materials. In a further aspect, a polymerization inhibitor can be present in the distilling vessel of the distillation. In a yet further aspect, a polymerization inhibitor can be selected so as to undergo volatization during the distillation process. In an even further aspect, a polymerization inhibitor can be selected so as to not volatize during the distillation process. In a still further aspect, a polymerization inhibitor can be present in the receiving vessel of the distillation.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. Unless explicitly disclosed, this disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, for example 1 to 12 carbon atoms or 1 to 6 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. A "lower alkyl" group is an alkyl group containing from one to six carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$—$OA^2$ or —$OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C═C. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula $NA^1A^2A^3$, where $A^1$, $A^2$, and $A^3$ can be, independently, hydrogen or substituted or unsubstituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)$A^1$ or —C(O)O$A^1$, where $A^1$ can be a substituted or unsubstituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer from 1 to 500. "Polyester" is the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halide" and "halo" as used herein refer to the halogens fluorine, chlorine, bromine, and iodine.

The terms "hydroxyl" and "hydroxyl" as used herein is represented by the formula —OH.

The term "ketone" and "keto" as used herein is represented by the formula $A^1C(O)A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The terms "nitrile" and "cyano" as used herein are represented by the formula —CN.

The term "silyl" as used herein is represented by the formula —$SiA^1A^2A^3$, where $A^1$, $A^2$, and $A^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2OA^1$, where $A^1$ can be hydrogen or a substituted or unsubstituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or a substituted or unsubstituted alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, a substituted or unsubstituted alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, a substituted or unsubstituted alkyl, cycloalkyl, alkenyl, cycloalkenyl, alkynyl, cycloalkynyl, aryl, or heteroaryl group as described herein.

The term "thiol" as used herein is represented by the formula —SH.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to acryloyl compounds comprising the structure:

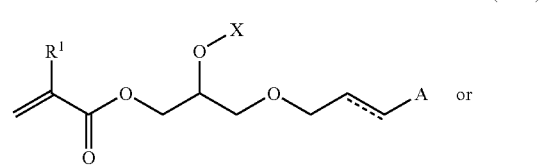

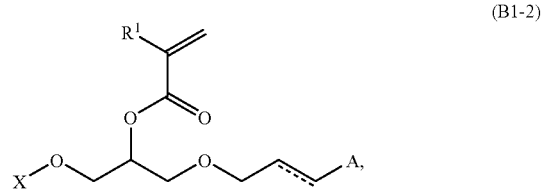

wherein R$^1$ is hydrogen, C$_1$-C$_{18}$ alkyl, or phenyl; wherein X is hydrogen or a hydrolysable group; wherein A is hydrogen and - - - is a double bond, or wherein A comprises a siloxanyl group and - - - is a single bond; and wherein X and A are not simultaneously hydrogen. In a further aspect, R$^1$, X, and A are not simultaneously methyl, hydrogen, and hydrogen, respectively. In a yet further aspect, X is not hydrogen. In a further aspect, X is a hydrolysable group and comprises alkyl, acyl, or silyl. In a further aspect, R$^1$ is hydrogen or methyl.

In one aspect, X is a hydrolysable alkyl group selected from a residue of dihydropyran, a residue of alkyl halide, a residue of tosyloxyalkane, a residue of diazoalkane, and a residue of dialkyl sulfate. In a further aspect, X is a hydrolysable acyl group selected from a residue of an acid anhydride and a residue of an acid halide. In a yet further aspect, X is a hydrolysable silyl group selected from a residue of a halogenated silane and a residue of a silazane.

"A" is typically a siloxanyl group or moiety; however, it is understood that, in one aspect, in the compounds and compositions of the invention, the A moiety is not necessarily limited to any particular siloxanyl group, but can be any siloxanyl group derived from an compound having a formula A-H and capable of undergoing a hydrosilyaltion reaction. That is, in one aspect, a silane compound (i.e, a compound having at least one silicon-hydrogen bond) that can undergo a hydrosilyaltion reaction can react to provide an "A" moiety or residue.

In one aspect, a material for producing molded plastics is provided, which material comprises the compound represented by the following Formula (A1-1) or (A1-2):

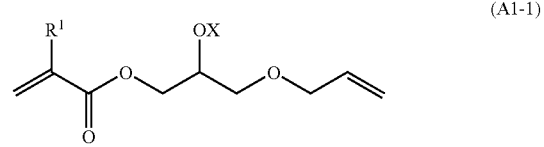

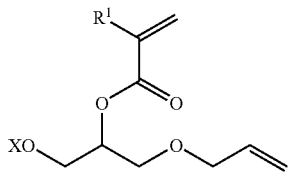
(A1-2)

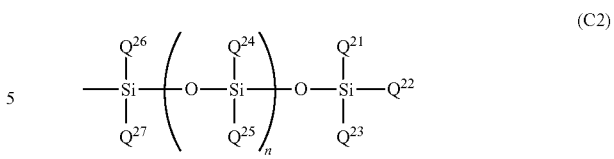
(C2)

wherein $R^1$ represents hydrogen or methyl; and X represents a hydrolyzable group.

In the Formulae (A1-1) and (A1-2), $R^1$ represents hydrogen or methyl, and $R^1$ is preferably methyl in view of chemical stability. X represents hydrogen or a hydrolyzable group, and preferred examples of X include hydrogen; pyranyl; alkyl groups such as methyl and t-butyl; acyl groups such as acetyl, formyl and propionyl; and silyl groups such as trimethylsilyl and t-butyldimethylsilyl. In cases where X is a hydrolyzable group, it is preferably an acyl or silyl, and most preferably silyl, from the viewpoint that it may easily be converted to hydroxyl group by hydrolysis or solvolysis.

The compound represented by the Formula (A1-2) or (A1-2) contained in the material for producing molded plastics according to the present invention is characterized in that the compound has an allyl group and a protected hydroxyl group in its molecule. Since the compound has an allyl group and (meth)acryloyl group, it serves as a cross-linking agent. Further, since the hydroxyl group is protected by a protective group, the compound also has a good compatibility with hydrophobic siloxanyl monomers.

Since the compound represented by the Formula (A1-2) or (A1-2) contained in the material for producing molded plastics according to the present invention has a hydroxyl group protected by a hydrolyzable group X, it is preferred to convert X to hydrogen by hydrolysis or solvolysis, thereby making the siloxanyl compound have a hydroxyl group. The conversion of X to hydrogen may be carried out after preparing molded plastics, or may be carried out at a stage prior to the polymerization for preparing the molded plastics. The latter is preferred because the compatibility with other hydrophilic polymeric material is promoted.

In Formulae (B1-1) and (B1-2), $R^1$ represents hydrogen or methyl, and X represents a hydrolyzable group. Preferred examples of $R^1$ and X are the same as those preferred in the above-described Formula (A1-1) or (A1-2), respectively. "A" represents a siloxanyl group, and preferred examples thereof are those represented by the following Formula (C1) or (C2):

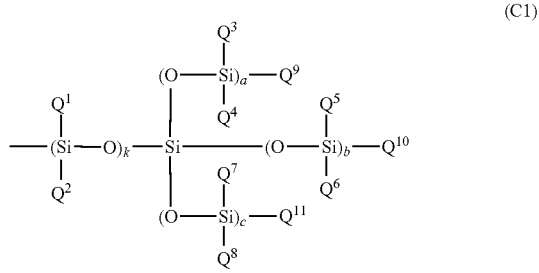
(C1)

wherein $Q^1$ to $Q^{11}$ independently represent hydrogen, $C_1$-$C_{20}$ alkyl which may be substituted or $C_6$-$C_{20}$ aryl which may be substituted; k represents an integer of 0 to 200; and a, b, and c independently represent integers of 0 to 20, with the proviso that all of k, a, b, and c are not simultaneously zero.

wherein $Q^{21}$ to $Q^{27}$ independently represent hydrogen, $C_1$-$C_{18}$ alkyl or phenyl; and n represents an integer of 2 to 12.

In the above-described Formula (C1), $Q^1$ to $Q^{11}$ independently represent hydrogen, $C_1$-$C_{20}$ alkyl which may be substituted or $C_6$-$C_{20}$ aryl which may be substituted, and specific examples thereof include hydrogen; alkyl groups such as methyl, ethyl, propyl, isopropyl, butyl, isobutyl, sec-butyl, t-butyl, hexyl, cyclohexyl, 2-ethylhexyl and octyl; and aryl groups such as phenyl and naphthyl. Among these, the most preferred is methyl group.

k represents an integer of 0 to 200, and preferably zero.

a, b, and c independently represent integers of 0 to 20 except for the case wherein k, a, b, and c are simultaneously zero, and preferably, a, b, and c independently represent integers of 0 or 1.

In the above-described Formula (C2), $Q^{21}$ to $Q^{27}$ independently represent hydrogen, $C_1$-$C_{18}$ alkyl or phenyl.

$Q^{21}$ is preferably hydrogen, methyl, ethyl, propyl, butyl, pentyl, hexyl, 2-ethylhexyl, octyl, decyl, undecyl, dodecyl, octadecyl, cyclopentyl, cyclohexyl, benzyl, phenyl or the like.

From the viewpoint of the chemical stability of the molded plastics to be obtained, methyl, ethyl, propyl and butyl are especially preferred.

$Q^{22}$ to $Q^{27}$ are preferably hydrogen, methyl, ethyl, propyl, butyl, pentyl, hexyl, 2-ethylhexyl, octyl, decyl, undecyl, dodecyl, octadecyl, cyclopentyl, cyclohexyl, benzyl, phenyl or the like. In view of the oxygen permeability, hydrophilicity and resistance to breakage of the molded plastics to be obtained, methyl group is most preferred.

n represents an integer of 2 to 12, and from the viewpoint of oxygen permeability, hydrophilicity and resistance to breakage of the molded plastics to be obtained, n is preferably an integer of 2 to 8, more preferably 3 to 6.

Among the groups represented by the above-described Formula (C1) or (C2), particularly preferred siloxanyl groups A are tris(trimethylsiloxy)silyl group, bis(trimethylsiloxy)methylsilyl group, trimethylsiloxydimethylsilyl group and the groups represented by the following Formula (C2-1).

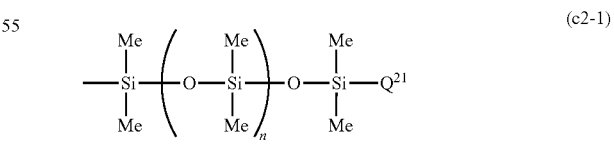
(c2-1)

wherein $Q^{21}$ represents the same meaning as $Q^{21}$ in the above-described Formula (C2).

A preferred process for producing the siloxanyl compound represented by A-H when A is a group represented by the above-described Formula (C2), that is, the compound represented by the following Formula (D1) will now be described.

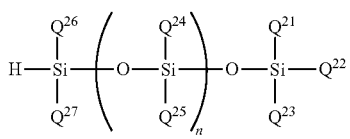
(D1)

First, a compound represented by the Formula $Q^{21}Li$ and a compound represented by the following Formula (E1) are reacted in an aprotic solvent (Step 1).

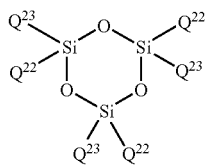
(E1)

The molar ratio of the compound represented by the Formula $Q^{21}Li$ to the compound represented by the Formula (E1) is preferably from about 0.1:1 to about 5:1, more preferably from about 0.2:1 to about 3.5:1. The reaction temperature is preferably from about −50° C. to about 50° C., more preferably from about −20° C. to about 40° C., still more preferably from about −10° C. to about 30° C. The reaction solvent is an aprotic solvent, and preferred examples thereof include aliphatic hydrocarbon solvents such as hexane, heptane, and petroleum benzine; aromatic hydrocarbon solvents such as toluene and xylene; and ether solvents such as tetrahydrofuran, diethyl ether, and ethylene glycol dimethylether. Two or more of these solvents may be used in combination. The reaction time is preferably from about 10 minutes to about 10 hours, more preferably from about 30 minutes to about 6 hours.

Then a compound represented by the following Formula (E2) is added to the reaction system, and the resulting mixture is allowed to further react (Step 2). However, Step 2 may be omitted. In cases where Step 2 is omitted, in the above-described Formula (D1), $Q^{24}$ represents the same substituent group as $Q^{22}$, and $Q^{25}$ represents the same substituent group as $Q^{23}$.

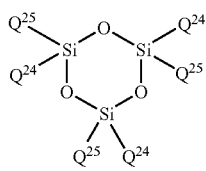
(E2)

In Step 2, the molar ratio of the compound represented by Formula $Q^{21}Li$ used in Step 1 to the compound represented by Formula (E2) is preferably 0.1:1 to 5:1, more preferably 0.2:1 to 3.5:1. The compound represented by Formula (E2) can be added in the form of a solution dissolved in an aprotic solvent. Preferred examples of the solvent used therefor are the same as the reaction solvent used in Step 1. The reaction temperature is preferably from about −50° C. to about 50° C., more preferably from about −20° C. to about 40° C., still more preferably from about −10° C. to about 30° C. The reaction time is preferably from about 10 minutes to about 10 hours, more preferably from about 30 minutes to about 6 hours.

Thereafter, a compound represented by the following Formula (E3) is added to the reaction system, and the resulting mixture is allowed to further react (Step 3).

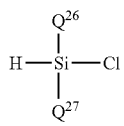
(E3)

In Step 3, the molar ratio of the compound represented by the Formula $Q^{21}Li$ used in Step 1 to the compound represented by the Formula (E3) is preferably from about 0.2:1 to about 5:1, more preferably from about 0.5:1 to about 2:1. The compound of the Formula (E3) may be added in the form of a solution dissolved in an aprotic solvent. Preferred examples of the solvent used therefor are the same as the reaction solvent used in Step 1. The reaction temperature is preferably from about −50° C. to about 50° C., more preferably from about −10° C. to about 40° C., still more preferably from about 0° C. to about 30° C. The reaction time is preferably from about 10 minutes to about 10 hours, more preferably from about 30 minutes to about 6 hours.

By the above-described operations, a crude compound represented by Formula (D1) is obtained. This compound is then purified by a purification method such as distillation method or column chromatography method. As the purification method, distillation method is most preferred.

The symbols in the above-described Formulae (D1), (E1), (E2) and (E3) represent the same meanings as the corresponding symbols in the above-described Formulae (A1-1), (A1-2), (B1-1) and (B1-2).

1. Branched Siloxanyl Groups

In one aspect, A comprises a siloxanyl group comprising the structure:

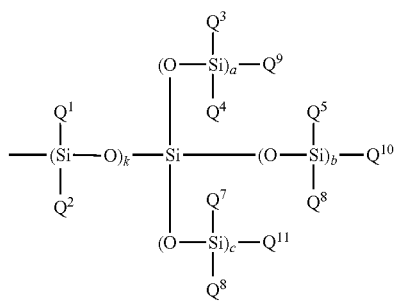

and - - - is a single bond, wherein $Q^1$ to $Q^{11}$ independently represent hydrogen, substituted or unsubstituted $C_1$-$C_{20}$ alkyl, or substituted or unsubstituted $C_6$-$C_{20}$ aryl; wherein k represents an integer of 0 to 200; and wherein a, b, and c independently represent integers of 0 to 20, with the proviso that all of k, a, b, and c are not simultaneously zero.

In further aspects, k can be 0 to 100, 0 to 50, 0 to 20, 0 to 10, 1 to 100, 1 to 50, 1 to 20, 1 to 10, less than 100, less than 50, less than 20, less than 10, 10, 9, 8, 7, 6, 5, 4, 3, 2, 1, or 0. In one aspect, k is 0.

In certain aspects, $Q^1$ to $Q^{11}$ are independently methyl. In a further aspect, $Q^1$ to $Q^{11}$ are simultaneously methyl.

In certain aspects, a, b, and c independently represent integers of 0 or 1. In further aspects, a, b, and c simultaneously represent integers of 0. In further aspects, a, b, and c simultaneously represent integers of 1.

2. Linear Siloxanyl Groups

In one aspect, A comprises a siloxanyl group comprising the structure;

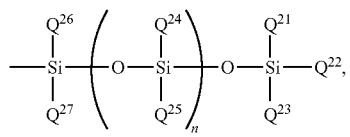

and - - - is a single bond, wherein $Q^{21}$ to $Q^{27}$ independently represent hydrogen, $C_1$-$C_{18}$ alkyl, or phenyl; and wherein n represents an integer of 2 to 12.

In certain aspects, $Q^{21}$ is methyl, ethyl, propyl, or butyl. In further aspects, $Q^{22}$ to $Q^{27}$ are independently hydrogen, methyl, ethyl, propyl, butyl, pentyl, hexyl, 2-ethylhexyl, octyl, decyl, undecyl, dodecyl, octadecyl, cyclopentyl, cyclohexyl, benzyl, or phenyl.

In various further aspects, n is from 2 to 8, 2 to 6, 4 to 8, 2, 3, 4, 5, 6, 7, or 8.

C. Compositions

In one aspect, the invention relates to compositions comprising a compound of the invention or a hydrolysis product thereof. In a further aspect, a composition of the invention can comprise a polymer comprising residues of a compound of the invention or a hydrolysis product thereof. In a yet further aspect, the polymer is a copolymer comprising residues of from at least one hydrophilic monomer. For example, the copolymer can comprise one or more residues of 2-hydroxyethyl methacrylate.

In a further aspect, the composition comprises at least two siloxanyl compounds and at least a portion of the compounds are cross-linked. In a yet further aspect, the cross-linked compounds form a polymer.

1. Mode

It is understood that a composition comprising compounds comprising a variable number of residues, for example a polymer or an oligomer, can have a distribution of molecular weights resulting from the varying number of residues among individual molecules. That is, the individual molecules of the compound in the composition can have different degrees of polymerization (DP). Such a distribution can have an average number of residues that can be described by the mean, median, or mode.

For example, in the acryloyl compounds of the invention, a number of residues can be described by "n," wherein n represents an integer of 0 or more. In the compositions of the invention, for example, the individual molecules of the compound can have a mode. For example, the mode can be from about 2 to about 9, from about 3 to about 6, from about 4 to about 8, from about 2 to about 5, from about 3 to about 7, about 2, about 3, about 4, about 5, about 6, about 7, about 8, or about 9.

2. Purity

In one aspect, the compositions can be provided having a high purity. That is, the compositions can have a relatively low concentration of undesirable impurities. Undesirable impurities can include, for example, epoxide or diol moieties that can have irritating properties when the compositions are used as contact lenses and intraocular lenses.

In certain aspects, an undesirable impurity, for example an epoxide moiety or a diol moiety, is present in a concentration of less than about 100 ppm, less than about 80 ppm, less than about 60 ppm, less than about 40 ppm, less than about 20 ppm, or less than about 10 ppm. In a further aspect, an undesirable impurity, for example an epoxide moiety or a diol moiety, is substantially absent from the composition.

Without wishing to be bound by theory, it is believed that by avoiding an epoxide-functionalized reagent in the final preparation step, the amount or concentration of undesirable epoxide or diol impurities can be minimized or eliminated from the compositions.

D. Applications of the Compositions

The present invention provides a material from which molded plastics having a satisfactory oxygen permeability, satisfactory hydrophilicity and satisfactory resistance to breakage may be produced by polymerizing the material. The molded plastics are useful as drug adsorbents used for drug delivery, and ophthalmic lenses such as contact lenses, intraocular lenses, artificial cornea and spectacle lenses. Among these, they are particularly suited for contact lenses.

In one aspect, the compositions can provide materials for producing molded plastics, which material is excellent in compatibility with hydrophilic monomers such as 2-hydroxyethyl methacrylate, which is capable of yielding molded plastics, by polymerizing the material, having satisfactory oxygen permeability, satisfactory hydrophilicity, and a low modulus of elasticity, as well as excellent optical quality.

By the present invention, a material for producing molded plastics may be provided, which material is excellent in compatibility with hydrophilic monomers such as, but not limited to 2-hydroxyethyl methacrylate, N-vinyl pyrrolidone, N,N-dimethylacrylamide, N-vinyl-N-methyl acetamide combinations thereof and the like which is capable of yielding molded plastics, by polymerizing the material, having a satisfactory oxygen permeability, satisfactory hydrophilicity and a low modulus of elasticity, as well as excellent optical quality.

In one aspect, the compounds and compositions of the invention can be used to provide a molded article comprising at least one of the compositions of the invention. In a further aspect, the compounds and compositions of the invention can be used to provide an ophthalmic lens comprising at least one of the compositions of the invention. In a yet further aspect, the compounds and compositions of the invention can be used to provide a contact lens comprising at least one of the compositions of the invention.

E. Methods of Making the Compounds

In one aspect, the invention relates to methods of synthesizing an acryloyl compound, comprising the step of hydrosilylating a first compound having the structure:

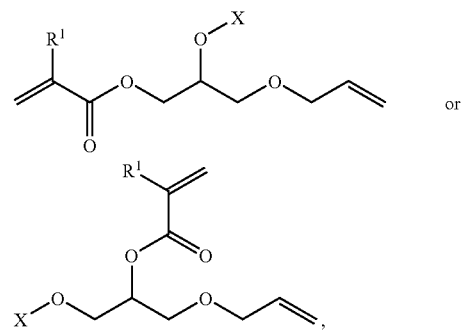

wherein $R^1$ represents hydrogen, $C_1$-$C_{18}$ alkyl, or phenyl, and wherein X represent hydrogen or a hydrolysable group; with a second compound having the structure A-H, wherein A comprises a siloxanyl group, to yield a third compound having the structure:

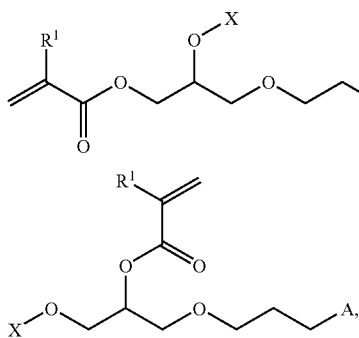

wherein X is hydrogen or a hydrolysable group; and wherein A is a siloxanyl group.

The disclosed methods can be optionally performed under an inert gas atmosphere. For example, the atmosphere can be nitrogen, helium, or argon.

It is understood that, in one aspect, that, in the methods of the invention, the A moiety is not necessarily limited to any particular siloxanyl group, but can be any siloxanyl group derived from an A-H compound and capable of undergoing a hydrosilyaltion reaction.

In one aspect, a process of producing a material for producing molded plastics is provided, which process comprises reacting the compound represented by the above-described Formula (A1-1) or (A1-2) with a siloxanyl compound having at least one hydrogen-silicon bond in its molecule to obtain a material for producing molded plastics, represented by the following Formula (B1-1) or (B1-2):

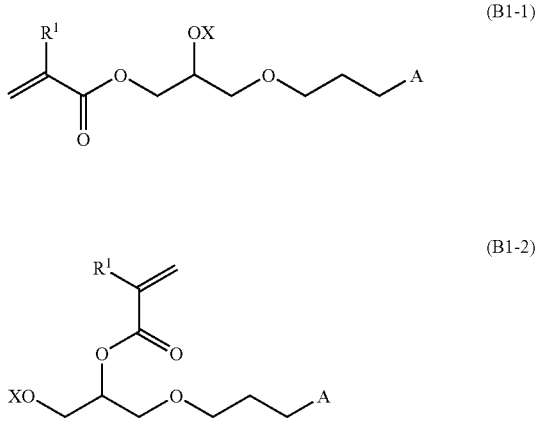

wherein $R^1$ represents hydrogen or methyl; X represents a hydrolyzable group; and A represents a siloxanyl group.

Typically, methods employing an epoxide-functionalized reagent in the final preparation step are avoided, thereby minimizing or eliminating the amount or concentration of undesirable epoxide or diol impurities in the compositions.

In one aspect, the hydrosilylation step is performed in the presence of a polymerization inhibitor or a radical scavenger.

In a further aspect, the siloxanyl group comprises the structure:

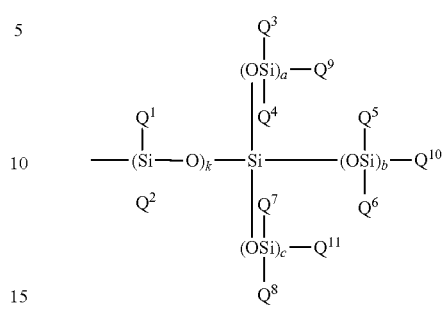

wherein $Q^1$ to $Q^{11}$ independently represent hydrogen, substituted or unsubstituted $C_1$-$C_{20}$ alkyl, or substituted or unsubstituted $C_6$-$C_{20}$ aryl; wherein k represents an integer of 0 to 200; and wherein a, b, and c independently represent integers of 0 to 20, with the proviso that all of k, a, b, and c are not simultaneously zero.

In a further aspect, the siloxanyl group comprises the structure;

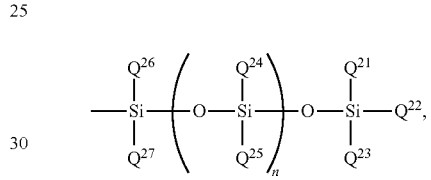

wherein $Q^{21}$ to $Q^{27}$ independently represent hydrogen, $C_1$-$C_{18}$ alkyl, or phenyl; and wherein n represents an integer of 2 to 12.

In a further aspect, X is a hydrolysable group, and the method further comprises the step of hydrolyzing or solvolyzing the third compound to yield a fourth compound having the structure:

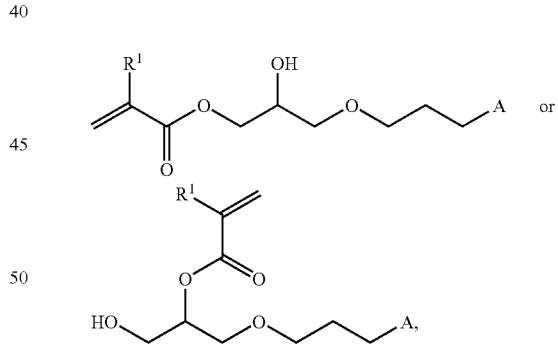

In one aspect, a process of producing a material for producing molded plastics is provided, which process comprises hydrolyzing or solvolyzing the compound represented by the above-described Formula (B1-1) or (B1-2) to obtain a material for producing molded plastics, represented by the following Formula (B2-1) or (B2-2):

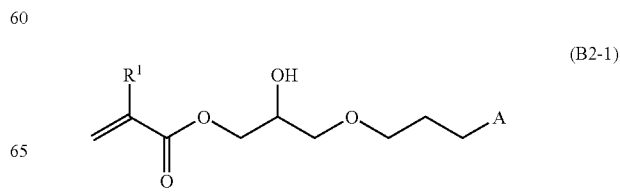

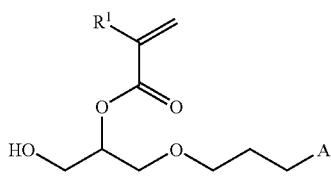
(B2-2)

wherein $R^1$ represents hydrogen or methyl; and A represents a siloxanyl group.

In a further aspect, the method further comprises the step of providing the first compound by treating allyl glycidyl ether with an alkylacrylic acid to yield a starting compound having the structure:

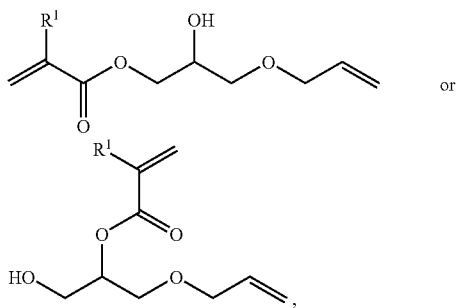

optionally in the presence of a polymerization inhibitor or a radical scavenger, wherein $R^1$ represents hydrogen, $C_1$-$C_{18}$ alkyl, or phenyl; and optionally protecting the hydroxyl group with a protecting reagent to yield a second compound having the structure:

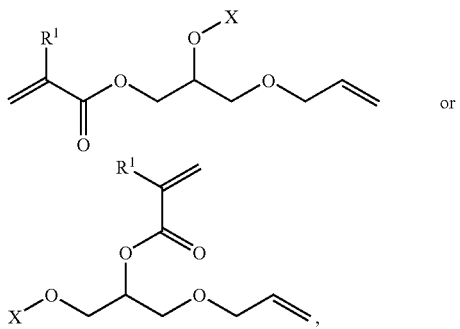

wherein X is a hydrolysable group.

In a yet further aspect, $R^1$ is hydrogen or methyl.

In a still further aspect, the protecting reagent is an alkylating agent, an acylating agent, or a silylating agent. In one aspect, X is a hydrolysable alkyl group selected from a residue of dihydropyran, a residue of alkyl halide, a residue of tosyloxyalkane, a residue of diazoalkane, and a residue of dialkyl sulfate. In a further aspect, X is a hydrolysable acyl group selected from a residue of an acid anhydride and a residue of an acid halide. In a yet further aspect, X is a hydrolysable silyl group selected from a residue of a halogenated silane and a residue of a silazane.

The material for producing molded plastics, which comprises a compound represented by the Formula (B1-1) or (B1-2) may be produced by reacting a compound represented by the above-described Formula (A1-1) or (A1-2) with the compound represented by Formula H-A in the presence of the catalyst for hydrosilylation reaction (Step #1).

In Step #1, the molar ratio of the compound represented by Formula (A1-1) or ($A^1$-2) (in cases where the compounds represented by these Formulae are contained, the total amount) to the compound represented by the Formula H-A is preferably from about 0.5:1 to about 10:1, more preferably from about 0.8:1 to about 5:1, still more preferably from about 1:1 to about 3:1. In Step #1, it is preferred to use a noble metal-based hydrosilylation catalyst. As the noble metal-based hydrosilylation catalyst, known catalysts usually used for hydrosilylation reaction may be employed. Examples of the catalyst include particulate platinum, particulate platinum carried by carbon powder, chloroplatinic acid, alcohol-modified chloroplatinic acid, olefin complex of chloroplatinic acid, coordination compound between chloroplatinic acid and vinyl siloxane, platinum black, tetrakis(triphenylphosphine)palladium, palladium black and rhodium catalyst. In case of a homogenous catalyst, the amount of the catalyst is preferably from about 0.1 ppm to about 100 ppm based on the total weight of the compound represented by the Formula (A1-1) or ($A^1$-2) and the compound of the Formula H-A, and in case of a heterogeneous catalyst, the amount of the catalyst is preferably from about 20 ppm to about 2000 ppm based on the total weight of the compound represented by the Formula (A1-1) or (A1-2) and the compound of the Formula H-A. The reaction may be carried out in a solvent or may be carried out without a solvent. Industrially, it is most preferred to carry out the reaction without a solvent. Preferred examples of the solvent are the same as those of the reaction solvent used in Step 1. The reaction temperature is preferably from about −10° C. to about 150° C., more preferably from about 20° C. to about 120° C. The reaction time is preferably from about 10 minutes to about 10 hours, more preferably from about 30 minutes to about 6 hours.

By the above-described operations, the material for producing molded plastics, which is at least one compound represented by the Formula (B1-1) or (B1-2) is obtained. Use of a heterogeneous catalyst is preferred because the catalyst may be removed by filtration at this stage.

It is preferred to remove the residual materials and low-boiling impurities at this stage as required by heating the product under reduced pressure. From the viewpoint of the efficiency of removal of these materials and purity of the product, the heating may preferably be carried out at a temperature from about 60° C. to about 160° C.

Further, as required, the product may be purified by a purification method such as distillation method or column chromatography method. As the purification method, column chromatography method is preferred. The column chromatography may preferably be carried out using porous particles. The porous particles may be one type of particles, or two or more types of particles may be used in combination. A solvent may be used in the purification. Examples of such solvents include various alcohols such as methanol, ethanol, propanol, 2-propanol, butanol, ethylene glycol, diethylene glycol, triethylene glycol, tetraethylene glycol, polyethylene glycol, and glycerin; various aromatic hydrocarbons such as benzene, toluene, and xylene; various aliphatic hydrocarbons such as hexane, heptane, octane, decane, petroleum ether, kerosene, ligroin, and paraffin; various ketones such as acetone, methyl ethyl ketone, and methyl isobutyl ketone; various esters such as ethyl acetate, butyl acetate, methyl benzoate, and dioctyl phthalate; various ethers such as diethyl ether, tetrahydrofuran, dioxane, ethylene glycol dialkyl ether, diethylene glycol dialkyl ether, triethylene glycol dialkyl ether, tetraethylene glycol dialkyl ether, and polyethylene glycol dialkyl ether; various aprotic polar solvents such as dimethylformamide, dimethylacetamide, N-methyl-2-pyrrolidone, dimethylimidazolidinone, hexamethylphosphoric triamide, and dimethyl sulfoxide; halogen-containing solvents such as methylene chloride, chloroform, dichloroethane, trichloroethane, and trichloroethylene; and fluorocarbon solvents. The solvent may be used individually, or two or more solvents may be used in combination.

A process of producing the material for producing molded plastics, which material comprises the compound represented by the Formula (B2-1) or (B2-2) will now be described.

The compound represented by the Formula (B2-1) or (B2-2) contained in the material for producing molded plastics, may be synthesized by hydrolyzing or solvolyzing the compound represented by the Formula (B1-1) or (B1-2) to remove X which is a protective group of the hydroxyl group, thereby converting the protected group to hydroxyl group (Step #2).

In Step #2, hydrolysis or solvolysis can be carried out by adding water or an active hydrogen-containing organic solvent in an amount approximately equivalent or excess to the protective group X. Preferred examples of the active hydrogen-containing organic solvent include various alcohols such as methanol, ethanol, propanol, 2-propanol, butanol, and t-amyl alcohol; various carboxylic acids such as formic acid, acetic acid, propionic acid, and terephthalic acid; various thiols; and various amines. Among these, alcohols and carboxylic acids are more preferred.

In Step #2, the reaction may be facilitated by adding a catalyst. Preferred examples of such catalysts include various inorganic acids such as hydrochloric acid and sulfuric acid; various sulfonic acids such as p-toluenesulfonic acid, methanesulfonic acid, and trifluoromethanesulfonic acid; various carboxylic acids such as formic acid, acetic acid, and propionic acid; various inorganic bases such as sodium hydroxide and sodium hydrogen carbonate; various salts such as sodium acetate and potassium acetate; and various organic bases such as triethylamine. Among these, inorganic acids, carboxylic acids, and sulfonic acids are more preferred.

From the viewpoint of reaction efficiency and maintenance of purity, the reaction temperature is preferably from about −20° C. to about 120° C., more preferably from about 10° C. to about 100° C., still more preferably from about 20° C. to about 70° C. The reaction time is preferably from about 1 minute to about 10 hours, more preferably from about 10 minutes to about 6 hours.

By the above-described operations, the material for producing molded plastics, which comprises the compound represented by the Formula (B2-1) or (B2-2) is obtained.

Then the aqueous reagents and impurities are preferably removed by washing with water and subsequent separation. The washing with water may be carried out by using aqueous solution or water appropriately selected from the group consisting of aqueous basic solution, aqueous acidic solution, aqueous neutral solution and water.

It is preferred to remove the residual materials and low-boiling impurities at this stage as required by heating the product under reduced pressure. From the viewpoint of the efficiency of removal of these materials and maintenance of purity, the heating may preferably be carried out at a temperature from about 0° C. to about 100° C.

The compound may preferably be purified by column chromatography or distillation under reduced pressure, and the latter is preferred. The column chromatography may preferably be carried out using porous particles. One type of porous particles may be used, or two or more types of porous particles may be used in combination. In the purification process, a solvent may be used. Examples of the solvent include various alcohols such as methanol, ethanol, propanol, 2-propanol, butanol, ethylene glycol, diethylene glycol, triethylene glycol, tetraethylene glycol, polyethylene glycol, and glycerin; various aromatic hydrocarbons such as benzene, toluene, and xylene; various aliphatic hydrocarbons such as hexane, heptane, octane, decane, petroleum ether, kerosene, ligroin, and paraffin; various ketones such as acetone, methyl ethyl ketone, and methyl isobutyl ketone; various esters such as ethyl acetate, butyl acetate, methyl benzoate, and dioctyl phthalate; various ethers such as diethyl ether, tetrahydrofuran, dioxane, ethylene glycol dialkyl ether, diethylene glycol dialkyl ether, triethylene glycol dialkyl ether, tetraethylene glycol dialkyl ether, and polyethylene glycol dialkyl ether; various aprotic polar solvents such as dimethylformamide, dimethylacetamide, N-methyl-2-pyrrolidone, dimethylimidazolidinone, hexamethylphosphoric triamide, and dimethyl sulfoxide; halogen-containing solvents such as methylene chloride, chloroform, dichloroethane, trichloroethane, and trichloroethylene; and fluorocarbon solvents. These solvents may be used individually or two or more of these solvents may be used in combination.

In a further aspect, the invention relates to methods of producing a siloxanyl monomer comprising a structure:

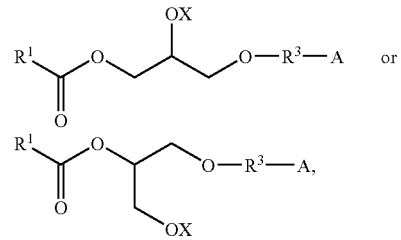

wherein $R^1$ represents a $C_1$-$C_{20}$ substituent having at least one unsaturated bond, wherein $R^3$ represents a $C_1$-$C_7$ divalent substituent, wherein A represents a siloxanyl group, and wherein X represents a hydrogen or a hydrolyzable group; the method comprising the step of reacting an unsaturated compound having a structure:

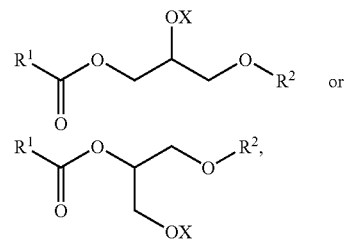

wherein $R^1$ represents a $C_1$-$C_{20}$ substituent having at least one unsaturated bond, wherein $R^2$ represents a $C_1$-$C_7$ substituent having at least one unsaturated bond, and wherein X represents a hydrogen or a hydrolyzable group; with a siloxanyl compound having a structure A-H, wherein A represents a siloxanyl group, in the presence of a metal catalyst, thereby producing a reaction mixture containing a siloxanyl monomer; wherein the molar ratio of the unsaturated compound to the siloxanyl compound is from about 1.15:1 to about 10:1 during the reacting step.

1. Molar Ratio

In a yet further aspect, the various reagents used in the disclosed methods can be provided and used in amounts to improve the purity and yield of the resultant product. That is, in one aspect, the invention relates to selecting reagent stoichiometry to optimize product purity and yield. For example, the molar ratio of the unsaturated compound to the siloxanyl compound can be from about 1.15:1 to about 10:1, from about 1.2:1 to about 5:1, from about 1.5:1 to about 3:1, about 2:1, or about 2.5:1 during the reacting step.

2. Unsaturated Compounds

In one aspect, the disclosed methods can employ an unsaturated compound having a structure:

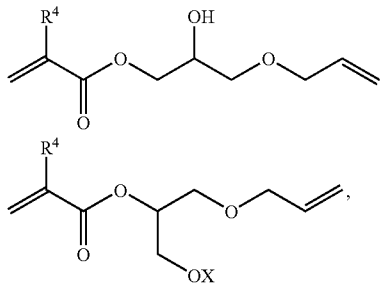

wherein $R^4$ is a hydrogen or a substituent selected from $C_1$-$C_{18}$ alkyl and phenyl; and wherein X is hydrogen or a hydrolyzable group; and wherein the siloxanyl monomer has a structure:

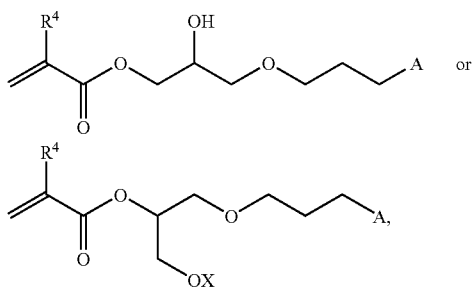

wherein $R^4$ is a hydrogen or a substituent selected from $C_1$-$C_{18}$ alkyl and phenyl; wherein A is a siloxanyl group; and wherein X is a hydrogen or a hydrolyzable group.

3. Siloxanyl Compounds

In a further aspect, the disclosed methods can employ a siloxanyl compound has a structure:

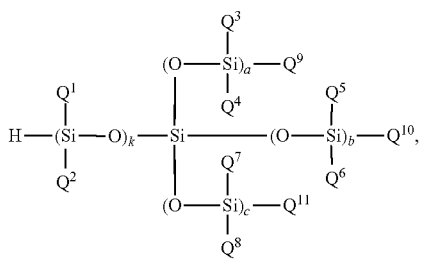

wherein $Q^1$ to $Q^{11}$ independently represent hydrogen or a substituent selected from $C_1$-$C_{20}$ alkyl which is optionally substituted and $C_6$-$C_{20}$ aryl which is optionally substituted; wherein k represents an integer of 0 to 200, for example 0 to 100, 0 to 50, 0 to 20, 0 to 10, 1 to 100, 1 to 50, 1 to 20, or 1 to 10, and wherein a, b, and c independently represent integers of 0 to 20, for example, 0 to 10, 1 to 10, 0 to 6, or 1 to 6, with the proviso that k, a, b, and c are not simultaneously zero.

In a yet further aspect, the siloxanyl compound can have a structure:

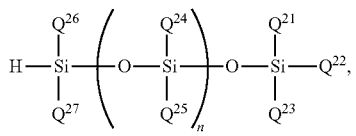

wherein $Q^{21}$ to $Q^{27}$ independently represent hydrogen or a substituent selected from $C_1$-$C_{18}$ alkyl and phenyl, and wherein n represents an integer of 0 to 12, for example, from 0 to 10, from 1 to 10, from 0 to 6, or from 1 to 6. In a still further aspect, the siloxanyl compound can have a structure:

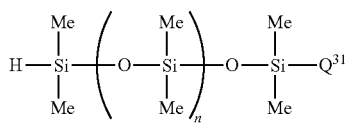

wherein $Q^{31}$ represents a substituent selected from $C_1$-$C_7$ alkyl and phenyl; and wherein n represents an integer of 1 to 10, for example, 1 to 8, 1 to 6, or 1 to 4.

Also disclosed are the products of the disclosed methods. The products can be provided as crude reaction products or, in a further aspect, can be purified to provide isolated products.

F. Purification

In one aspect, the need for extensive purification procedures can be minimized in the disclosed methods and for the disclosed compounds by controlling and inhibiting the generation of impurities by virtue of the appropriate selection of the reaction molar ratio between the starting materials. That is, the relative amounts of starting materials (e.g., unsaturated compounds and siloxanyl compounds) can be selected to minimize the production of impurities and/or to minimize the amount of residual unreacted starting materials. For example, if the reaction molar ratio is smaller than the disclosed ratios, the purity and/or yield of the desired product can be decreased. Likewise, if the reaction molar ratio is larger than the disclosed ratios, the purity and/or yield of the desired product can be decreased.

Conventional processes for producing siloxanyl monomers can suffer from unsatisfactory purity in the resultant siloxanyl monomer. Consequently, purification processes, including extraction and distillation, can be employed.

In one aspect, the disclosed methods can further comprise the sequential steps of mixing the reaction mixture with a hydrocarbon solvent and a hydrophilic solvent; allowing the mixture to form two layers; and separating the two layers, thereby removing the unsaturated compound from the reaction mixture. That is, an extraction process can be employed to remove impurities having differing solubility characteristics from the desired reaction product.

In one aspect, the hydrocarbon solvent is a $C_5$-$C_{25}$ aliphatic hydrocarbon solvent, for example, pentane, hexane, heptane, octane, nonane, decane, undecane, and dodecane. The solvent can be branched or unbranched, and the solvent can be cyclic or acyclic. It is also contemplated that mixtures of hydrocarbon solvents can be employed.

In one aspect, the hydrophilic solvent is a $C_1$-$C_5$ alcohol, for example, methanol, ethanol, propanol, butanol, or pentanol. The solvent can be branched or unbranched, and the solvent can be cyclic or acyclic. It is also contemplated that mixtures of hydrophilic solvents can be employed. In a further aspect, the hydrophilic solvent is water. In certain aspects, the hydrophilic solvent can be provided with an acidic or basic pH.

In certain aspects, the hydrocarbon solvent and the hydrophilic solvent are immiscible, thereby facilitating formation of two layers after mixing. In further aspects, the two solvents are partially miscible.

Although extraction can purify the reaction products from ionic or polar impurities while minimizing the risk of polymerization of the reaction products, conventional extraction techniques can be inefficient in separating the reaction products from nonionic and nonpolar impurities. In contrast, distillation can separate the reaction products from ionic or polar impurities as well as from nonionic and nonpolar impurities; however, conventional distillation techniques typically necessitate relatively high temperature when the molecular weights of the materials are large and, thus, can fail to minimize the risk of polymerization of the reaction products.

Consequently, disclosed methods can further comprise the step of removing the unsaturated compound from the reaction mixture by a distillation method, for example, short path distillation or thin film distillation. In certain aspects, such a distillation step can employ a polymerization inhibitor(s) in an amount of 50 ppm to 10,000 ppm, for example, from about 50 ppm to about 1,000 ppm, from about 50 ppm to about 500 ppm, from about 500 ppm to about 10,000 ppm, or from about 500 ppm to about 1,000 ppm, during the step of removing the product.

Suitable polymerization inhibitors include hydroquinone, p-methoxyphenol, di-t-butyl-p-cresol, pyrogallol, t-butyl catechol, benzoquinone, 4,4'-thiobis(3-methyl-6-t-butylphenol), 2,2'-methylenebis(4-methyl-6-t-butylphenol), and N-nitrosophenylhydroxylamine cerium (III) salt. Suitable polymerization inhibitors also include 2,2,6,6-tetramethyl-4-hydroxypiperidine-1-oxyl, N-nitrosophenyl hydroxylamine ammonium salt, N-nitrosophenyl hydroxylamine aluminum salt, N-nitroso-N-(1-naphthyl)hydroxylamine ammonium salt, N-nitrosodiphenylamine and N-nitroso-N-methylaniline. Suitable polymerization inhibitors also include nitroso compounds such as nitrosonaphthol, p-nitrosophenol and N,N'-dimethyl-p-nitrosoaniline; sulfur-containing compounds such as phenothiazine, Methylene Blue and 2-mercaptobenzimidazole; amines such as N,N'-diphenyl-p-phenylenediamine, N-phenyl-N'-isopropyl-p-phenylenediamine, 4-hydroxydiphenylamine and aminophenol; quinone compounds such as hydroxyquinoline, hydroquinone, methylhydroquinone, p-benzoquinone and hydroquinone monomethyl ether; phenol compounds such as methoxyphenol, 2,4-dimethyl-6-t-butylphenol, catechol, 3-s-butylcatechol and 2,2-methylenebis-(6-t-butyl-4-methylphenol); imides such as N-hydroxyphthalimide; oximes such as cyclohexane oxime and p-quinone dioxime; and dialkylthio dipropionates.

In a further aspect, a polymerization inhibitor can be a hydroxynaphthalene. The hydroxynaphthalene can be, for example, an alkoxy naphthol, a dihydroxynaphthol, or a dialkoxynaphthol. In one aspect, the hydroxynaphthalene is 4-methoxy-1-naphthol. In a further aspect, the at least one polymerization inhibitor comprises an alkylhydroquinone. The alkylhydroquinone can be, for example, 2-t-butylhydroquinone or 2,6-di-t-butylhydroquinone. In one aspect, the alkylhydroquinone is 2-t-butylhydroquinone. The alkyl group can comprise, for example, a substituted or unsubstituted $C_1$ to $C_{12}$ alkyl group. In one aspect, the alkyl group is selected from methyl, ethyl, propyl, butyl, pentyl, hexyl, heptyl, octyl, nonyl, decyl, undecyl, and dodecyl. In a further aspect, the alkyl group is a tertiary alkyl group.

G. Preparation of Molded Plastics

The molded plastics can be prepared by polymerizing the acryloyl compounds of the present invention (e.g., a material comprising the compound represented by the Formula (A1-1) or (A1-2), hereinafter referred to as "material A1"; a material comprising the compound represented by the Formula (B1-1) or (B1-2), hereinafter referred to as "material B1"; or a material comprising the compound represented by the Formula (B2-1) or (B2-2), hereinafter referred to as "material B2") either alone or with one or more other of the comonomers or materials described herein.

As the polymerizable materials which may be used for the copolymerization, monomers having a polymerizable carbon-carbon unsaturated bond such as (meth)acryloyl group, styryl group, allyl group, or vinyl group can be employed.

Preferred examples of such monomers include alkyl(meth) acrylates such as (meth)acrylic acid, itaconic acid, crotonic acid, cinnamic acid, vinylbenzoic acid, methyl (meth)acrylate and ethyl(meth)acrylate; polyfunctional (meth)acrylates such as polyalkylene glycol mono(meth)acrylate, polyalkylene glycol monoalkyl ether (meth)acrylate, polyalkylene glycol bis(meth)acrylate, trimethylolpropane tris(meth)acrylate, pentaerythritol tetrakis(meth)acrylate, polydimethyl siloxane having (meth)acryloxypropyl group at both ends, polydimethyl siloxane having (meth)acryloxypropyl group at one end and polydimethyl siloxane having a plurality of (meth)acryloyl groups in side chains; halogenated alkyl (meth)acrylates such as trifluoroethyl(meth)acrylate and hexafluoroisopropyl(meth)acrylate; hydroxyalkyl(meth) acrylates having hydroxyl group such as 2-hydroxyethyl (meth)acrylate, 2-hydroxypropyl(meth)acrylate and 2,3-dihydroxypropyl(meth)acrylate; (meth)acrylamides such as N,N-dimethylacrylamide, N,N-diethylacrylamide, N,N-di-n-propylacrylamide, N,N-diisopropylacrylamide, N,N-di-n-butylacrylamide, N-acryloylmorpholine, N-acryloylpiperidine, N-acryloylpyrrolidine and N-methyl(meth)acrylamide; N-vinyl-N-methyl acetamide, N-vinyl-N-ethyl acetamide, N-vinyl-N-ethyl formamide, N-vinyl formamide, aromatic vinyl monomers such as styrene, α-methylstyrene and vinylpyridine; maleimides; heterocyclic vinyl monomers such as N-vinylpyrrolidone; 3-[tris(trimethylsiloxy)silyl] propyl (meth)acrylate, 3-[bis(trimethylsiloxy)methylsilyl] propyl(meth)acrylate, 3-[(trimethylsiloxy)dimethylsilyl] propyl(meth)acrylate, 3-[tris(trimethylsiloxy)silyl]propyl (meth)acrylamide, 3-[bis(trimethylsiloxy)methylsilyl]propyl(meth)acrylamide, 3-[(trimethylsiloxy)dimethylsilyl]propyl(meth)acrylamide, [tris(trimethylsiloxy)silyl]methyl (meth)acrylate, [bis(trimethylsiloxy)methylsilyl]methyl (meth)acrylate, [(trimethylsiloxy)dimethylsilyl]methyl (meth)acrylate, [tris(trimethylsiloxy)silyl]methyl (meth) acrylamide, [bis(trimethylsiloxy)methylsilyl]methyl(meth) acrylamide, [(trimethylsiloxy)dimethylsilyl]methyl(meth) acrylamide, [tris(trimethylsiloxy)silyl]styrene, [bis (trimethylsiloxy)methylsilyl]styrene, [(trimethylsiloxy) dimethylsilyl]styrene, polydimethyl siloxane having (meth) acryloxypropyl group at one end, and compounds represented by Formula (C1-1) to (C6-1) and (C1-2) to (C6-2) below.

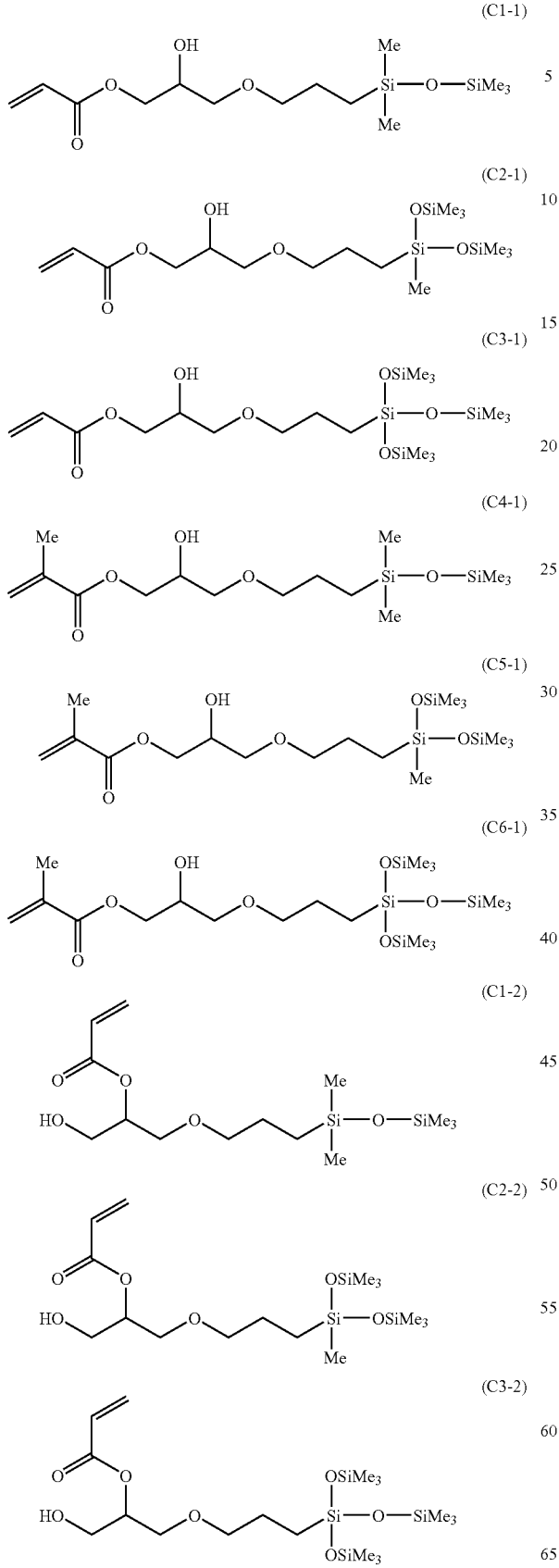
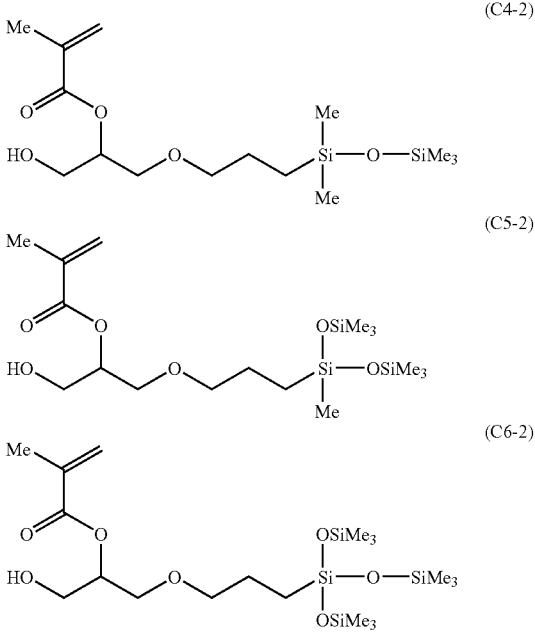

Other silicone containing components suitable for use in this invention include those described is WO 96/31792 such as macromers containing polysiloxane, polyalkylene ether, diisocyanate, polyfluorinated hydrocarbon, polyfluorinated ether and polysaccharide groups. U.S. Pat. Nos. 5,321,108; 5,387,662; and 5,539,016 describe polysiloxanes with a polar fluorinated graft or side group having a hydrogen atom attached to a terminal difluoro-substituted carbon atom. U.S. 2002/0016383 describe hydrophilic siloxanyl methacrylates containing ether and siloxanyl linkanges and crosslinkable monomers containing polyether and polysiloxanyl groups.

In one embodiment comonomers include (meth)acrylic acid, 2-hydroxyethyl (meth)acrylate, 2-hydroxypropyl (meth)acrylate, N,N-dimethylacrylamide, N-vinyl pyrrolidone, N-vinyl-N-methyl acetamide, N-vinyl-N-ethyl acetamide, 3-[tris(trimethylsiloxy)silyl]propyl(meth)acrylate, 3-[bis(trimethylsiloxy)methylsilyl]propyl (meth)acrylate, the compounds C1-1, C2-1, C3-1, C4-1, C5-1, C6-1, C1-2, C2-2, C3-2, C4-2, C5-2, C6-2, polysiloxane macromers, hydrophilic siloxyanly methacrlyates containing ether and siloxanyl linkages and combinations thereof and the like.

Further preferred examples of such monomers include 2-propenoic acid, 2-methyl-2-hydroxy-3-[3-[1,3,3,3-tetramethyl-1-[(trimethylsilyl)oxy]disiloxanyl]propoxy]propyl ester (SiGMA); monomethacryloxypropyl-terminated mono-n-butyl terminated polydimethylsiloxane (mPDMS; MW 800-1000 ($M_n$)); bis-3-acryloxy-2-hydroxypropyloxypropyl polydimethylsiloxane (acPDMS) (MW 1000 and 2000, acrylated polydimethylsiloxane from Gelest and Degussa, respectively); methacryloxypropyl-terminated polydimethylsiloxane (MW 550-700) from Gelest (maPDMS); and mono-(3-methacryloxy-2-hydroxypropyloxy) propyl terminated, mono-butyl terminated polydimethylsiloxane (mPDMS-OH).

For preparing the molded plastics, especially ophthalmic lenses, additional materials may also be included in the polymerization mixture. For example, a crosslinker having two or more polymerizable carbon-carbon unsaturated bonds in the molecule can be included to obtain good mechanical properties and good resistance to antiseptic solutions and washing solutions. The percentage of the crosslinker, based on the total monomers to be copolymerized, is preferably not less than about 0.01% by weight, more between about 0.05% and about 15% by weight, still more preferably between about 0.1% and about 5% by weight.

From the viewpoint of simultaneously attaining a satisfactory oxygen permeability and satisfactory hydrophilicity, the percentage of the material for producing molded plastics according to the present invention in the prepared molded plastics is, in cases where other siloxanyl-group containing polymerizable material is not copolymerized, preferably from about 30% by weight to about 100% by weight, more preferably from about 50% by weight to about 99% by weight, still more preferably from about 60% by weight to about 95% by weight. In cases where one or more other siloxanyl group-containing polymerizable materials are copolymerized, the percentage of the total of the material according to the present invention and the other siloxanyl group-containing polymerizable material(s) in the prepared molded plastics is preferably from about 30% by weight to about 100% by weight, more preferably from about 50% by weight to about 99% by weight, still more preferably from about 60% by weight to about 95% by weight.

The molded plastics may contain additional components, including, but not limited to UV absorbers, colorants, coloring agents, wetting agents, slip agents, pharmaceutical and nutraceutical components, compatibilizing components, antimicrobial compounds, release agents, combinations thereof and the like. Any of the foregoing may be incorporated in non-reactive, polymerizable, and/or copolymerized form.

In the (co)polymerization for preparing the molded plastics, it is preferred to add a thermal polymerization initiator or photopolymerization initiator typified by peroxides and azo compounds for easily attaining polymerization. In cases where thermal polymerization is carried out, one having the optimum decomposition characteristics at the satisfactory reaction temperature is selected. In general, azo initiators and peroxide initiators having a 10 hour half-life temperature of from about 40° C. to about 120° C. are preferred. Examples of the photoinitiator include carbonyl compounds, peroxides, azo compounds, sulfur compounds, halogenated compounds and metal salts. These polymerization initiators can be used individually or in combination. The amount of the polymerization initiator(s) can be up to about 1% by weight based on the polymerization mixture.

In (co)polymerizing the material for producing molded plastics according to the present invention, a polymerization solvent can be used. As the solvent, various organic and inorganic solvents can be employed. Examples of the solvents include water; alcoholic solvents such as methyl alcohol, ethyl alcohol, normal propyl alcohol, isopropyl alcohol, normal butyl alcohol, isobutyl alcohol, tert-butyl alcohol, ethylene glycol, diethylene glycol, triethylene glycol, tetraethylene glycol and polyethylene glycol; glycol ether solvents such as methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether and polyethylene glycol dimethyl ether; ester solvents such as ethyl acetate, butyl acetate, amyl acetate, ethyl lactate and methyl benzoate; aliphatic hydrocarbon solvents such as normal hexane, normal heptane and normal octane; alicyclic hydrocarbon solvents such as cyclohexane and ethylcyclohexane; ketone solvents such as acetone, methyl ethyl ketone and methyl isobutyl ketone; aromatic hydrocarbon solvents such as benzene, toluene and xylene; and petroleum solvents. These solvents can be used individually or two or more of these solvents can be used in combination.

As the method of polymerization of the material for producing molded plastics according to the present invention, and as the method of molding the plastics, known methods can be employed. For example, a method in which the material is once polymerized and molded into the shape of round bar or plate and the resulting round bar or plate is then processed into the satisfactory shape by cutting or the like, mold polymerization method and spin cast polymerization method can be employed.

As an example, a process for producing an ophthalmic lens by polymerizing the material composition containing the material for producing molded plastics according to the present invention by mold polymerization method will now be described.

First, a gap having a prescribed shape, between two mold parts is filled with the material composition and photopolymerization or thermal polymerization is carried out to shape the composition into the shape of the gap between the molds. The molds are made of a resin, glass, ceramics, metal, or the like. In case of photopolymerization, an optically transparent material is used, and a resin or glass is usually used. In case of producing an ophthalmic lens, a gap is formed between two mold parts facing each other, and the gap is filled with the material composition. Depending on the shape of the gap and on the properties of the material composition, a gasket may be used in order to give the ophthalmic lens a prescribed thickness and to prevent leakage of the material composition filled in the gap. The molds containing the gap filled with the material composition are then irradiated with an actinic radiation such as ultraviolet light, visible light or a combination thereof, or placed in an oven or bath to heat the material composition, thereby carrying out polymerization. The two polymerization methods may be employed in combination, that is, thermal polymerization may be carried out after photopolymerization, or photopolymerization may be carried out after thermal polymerization. In photopolymerization embodiment, a light containing ultraviolet light, such as the light from a mercury lamp or UV lamp (e.g., FL15BL, TOSHIBA corporation) is radiated for a short time (usually not longer than 1 hour). In cases where thermal polymerization is carried out, it is preferred to employ conditions in which the composition is slowly heated from room temperature to a temperature from about 60° C. to about 200° C. over a period of several hours to several tens hours, in view of the optical uniformity, high quality, and high reproducibility of the ophthalmic lens.

The molded plastics produced from the material of the present invention may preferably have a dynamic contact angle (during forward movement, immersion rate: about 0.1 mm/sec) of not more than about 130°, more preferably not more than about 120°, still more preferably not more than about 100°. The water content thereof is preferably from about 3% to about 50%, more preferably from about 5% to about 50%, still more preferably from about 7% to about 50%. From the viewpoint of the wearer when the ophthalmic lens is used as a contact lens, the higher the oxygen permeability, the better. The oxygen permeability coefficient $[\times 10^{-11} \, (cm^2/sec)mLO_2/(mL \cdot hPa)]$ is preferably not less than about 50, more preferably not less than about 60, still more preferably not less than about 65. The tensile modulus of elasticity is preferably from about 0.01 to about 30 MPa, more preferably from about 0.1 to about 7 MPa. The tensile elongation is preferably not less than about 50%, more preferably not less than about 100%. Since a higher tensile elongation gives higher resistance to breakage, it is preferred that the molded plastics have a high tensile elongation. These properties may be measured using the test methods disclosed in WO03/022321.

The molded plastics are useful as drug carriers used for drug delivery, and ophthalmic lenses such as contact lenses, intraocular lenses, artificial cornea, and spectacle lenses. Among these, they are particularly suited for ophthalmic lenses such as contact lenses, intraocular lenses, and artificial cornea. Among these, they are particularly suited for ophthalmic lenses, especially contact lenses.

H. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Synthesis of Acryloyl-Functionalized Compounds

First, acrylic acid or (meth)acrylic acid and allylglycidyl ether are reacted to synthesize the compound represented by the following Formula (A2-1) or (A2-2) (Step #1):

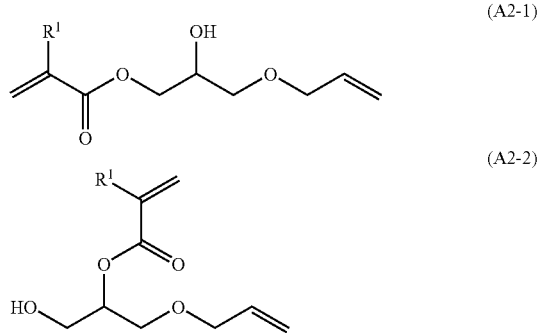

wherein $R^1$ represents hydrogen or methyl.

In Step #1, it is preferred to add a polymerization inhibitor or a radical scavenger in order to prevent gelation or solidification of the reaction medium during the synthesis reaction.

Preferred examples of the polymerization inhibitor include phenolic compounds such as hydroquinone, hydroquinone monomethyl ether, 2,6-di-t-butyl-4-methylphenol and 4-t-butylcatechol; and aluminum N-nitrosophenylhydroxylamine. The amount of the polymerization inhibitor is preferably 0.0005 to 30 mol %, more preferably 0.001 to 25 mol %, still more preferably 0.005 to 20 mol %, based on the amount of the (meth)acrylic acid.

Preferred examples of the radical scavenger include iodine, oxygen, nitrogen monoxide, hydrogen iodide, iron(III) chloride, anthracene, and α,α-diphenylpicrylhydrazyl. One or more polymerization inhibitors and one or more radical scavengers may also preferably be used in combination.

In cases where the radical scavenger is in the form of solid or liquid, the amount of the radical scavenger used in Step #1 is preferably 5 ppm to 50,000 ppm, more preferably 50 ppm to 40,000 ppm, still more preferably 100 ppm to 30,000 ppm, based on the (meth)acrylic acid used as a starting material. In cases where the radical scavenger is in the form of gas, it is preferred to bubble the reaction solution with a gas containing 0.1% to 100% of the scavenger, or to carry out the synthesis reaction under the atmosphere of the gas. In cases where oxygen is used as the scavenger gas, the oxygen concentration is preferably 0.1 to 100%, and in view of the balance between the explosion proof characteristics and the effect as a scavenger, it is more preferably 0.1 to 80%, still more preferably 0.1 to 60%. Since the air contains oxygen, the reaction may be carried out under bubbling with air or under air atmosphere.

The amount of (meth)acrylic acid used in Step #1 is preferably 1 to 20 equivalents, more preferably 2 to 12 equivalents, still more preferably 4 to 10 equivalents with respect to allylglycidyl ether. In Step #1, to accelerate the reaction, a catalyst may be added. Examples of the catalyst to be used include alkali (earth) metal hydroxides such as lithium hydroxide, sodium hydroxide, potassium hydroxide and calcium hydroxide; amines such as trimethylamine, triethylamine and pyridine; inorganic salts such as calcium carbonate and sodium hydrogen carbonate; alkali (earth) metal methacrylates such as lithium (meth)acrylate, sodium (meth)acrylate, potassium (meth)acrylate and calcium (meth)acrylate. The amount of the catalyst to be added is preferably 0.01 to 50 mol %, more preferably 0.05 to 40 mol %, still more preferably 0.1 to 30 mol % based on allylglycidyl ether.

The reaction temperature in Step #1 is preferably 50 to 180° C., more preferably 60 to 170° C., still more preferably 70 to 160° C.

In cases where the radical scavenger used in Step #1 is in the form of solid or liquid, it is preferred to remove the radical scavenger by an appropriate method after the reaction because it may influence on the polymerization of the produced siloxanyl monomer.

Then the aqueous starting materials and impurities are preferably removed by washing with water and subsequent separation. The washing with water may preferably be carried out by washing the reaction mixture several times with an aqueous basic solution such as aqueous sodium hydroxide solution, aqueous potassium hydroxide solution, or aqueous sodium hydrogen carbonate solution, and then with a neutral aqueous solution such as various buffers or aqueous sodium chloride solution, or with water.

The compound represented by the Formula (A2-1) or (A2-2) obtained in Step #1 may preferably be purified by column chromatography or distillation under reduced pressure, and the latter is preferred. The column chromatography may preferably be carried out using porous particles. In the present specification, the term "porous particle" means a particle having a number of pores in its surface. Specific examples of the porous particles include silica gel, active carbon, alumina, zeolite, and molecular sieve. One type of porous particles may be used, or two or more types of porous particles may be used in combination. In the purification process, a solvent may be used. Examples of the solvent include various alcohols such as methanol, ethanol, propanol, 2-propanol, butanol, ethylene glycol, diethylene glycol, triethylene glycol, tetraethylene glycol, polyethylene glycol, and glycerin; various aromatic hydrocarbons such as benzene, toluene, and xylene; various aliphatic hydrocarbons such as hexane, heptane, octane, decane, petroleum ether, kerosene, ligroin, and paraffin; various ketones such as acetone, methyl ethyl ketone, and methyl isobutyl ketone; various esters such as ethyl acetate, butyl acetate, methyl benzoate, and dioctyl phthalate; various ethers such as diethyl ether, tetrahydrofuran, dioxane, ethylene glycol dialkyl ether, diethylene glycol dialkyl ether, triethylene glycol dialkyl ether, tetraethylene glycol dialkyl ether, and polyethylene glycol dialkyl ether; various aprotic polar solvents such as dimethylformamide, dimethylacetamide, N-methyl-2-pyrrolidone, dimethylimidazolidinone, hexamethylphosphoric triamide and dimethyl sulfoxide; halogen-containing solvents such as methylene chloride, chloroform, dichloroethane, trichloroethane and trichloroethylene; and fluorocarbon solvents. These solvents may be used individually or two or more of these solvents may be used in combination.

The hydroxyl group in the compound represented by the Formula (A2-1) or (A2-2) (X in the formula is hydrogen) may be protected by a hydrolyzable group X by reacting the compound with an appropriate reagent, thereby the compound represented by the Formula (A1-1) or (A1-2) is obtained (Step #2).

Preferred examples of the reagent which may be used in Step #2 include alkylating agents such as dihydropyran, alkyl halide, tosyloxyalkane, diazoalkane, and dialkyl sulfate; acylating agents such as various acid anhydrides and various acid halides; and silylation agents such as halogenated silane and silazane.

2. Examples

The present invention will now be further described by way of examples.

a. Analysis

In the following Examples, the various measurements were carried out by the following methods:

Gas chromatography ("GC") was carried out under the following conditions: Apparatus and Parameters: Apparatus: Model GC6890 manufactured by HEWLETT-PACKARD or equivalent thereof. Detector: hydrogen flame ionization detector (FID). Column: Restek DB-1HT (30 m×0.25 mm×0.1 µm or equivalent). Carrier Gas: helium. Constant Flow: 1.0 mL/min. Amount of Applied Sample: 2.0 µL. Split Ratio: 30:1. Inlet Temperature: 300° C. Detector Temperature: 350° C. Solvent for Washing Autosampler: 2-propanol. Inlet Septum: Alltech 7/16" HT-X-11 or equivalent. Temperature Program: Initial Temperature: 100° C. Initial time: 2 min. Ramp: 15° C./min; Final Temp: 200° C.; hold for 0 min. Ramp: 5° C./min; Final Temp: 350° C.; hold for 0 min.; Ramp: 15° C./min; Final Temp: 400° C.; hold for 15 min. Sample Preparation: about 50 µL of a sample is dissolved in 1.0 mL of 2-propanol. The sample and 2-propanol are directly placed in a vial for GC and mixed therein. Calculation of Purity: Purity was calculated from the peak area of GC chromatogram.

GC-MS analysis was carried out by carrying out the GC analysis under the conditions described above and by using as a mass spectrometer JMS-DX303 manufactured by JEOL.

GPC was performed under the following conditions: Column: Shodex GPC K-801 and Shodex GPC K-802 manufactured by SHOKO CO., LTD. (each of them has an inner diameter of 8.0 mm and a length of 30 cm). The two columns were connected in series. Solvent: chloroform. Column Temperature: 40° C. Flow Rate: 1.0 mL/min. Apparatus: HLC-8022GPC manufactured by TOSOH CORPORATION, which is an integral apparatus combining a UV detector and a differential refractometer.

MALDI-TOFMS: AXIMA-CFR plus manufactured by SHIMADZU CORPORATION was used.

Figure 2:
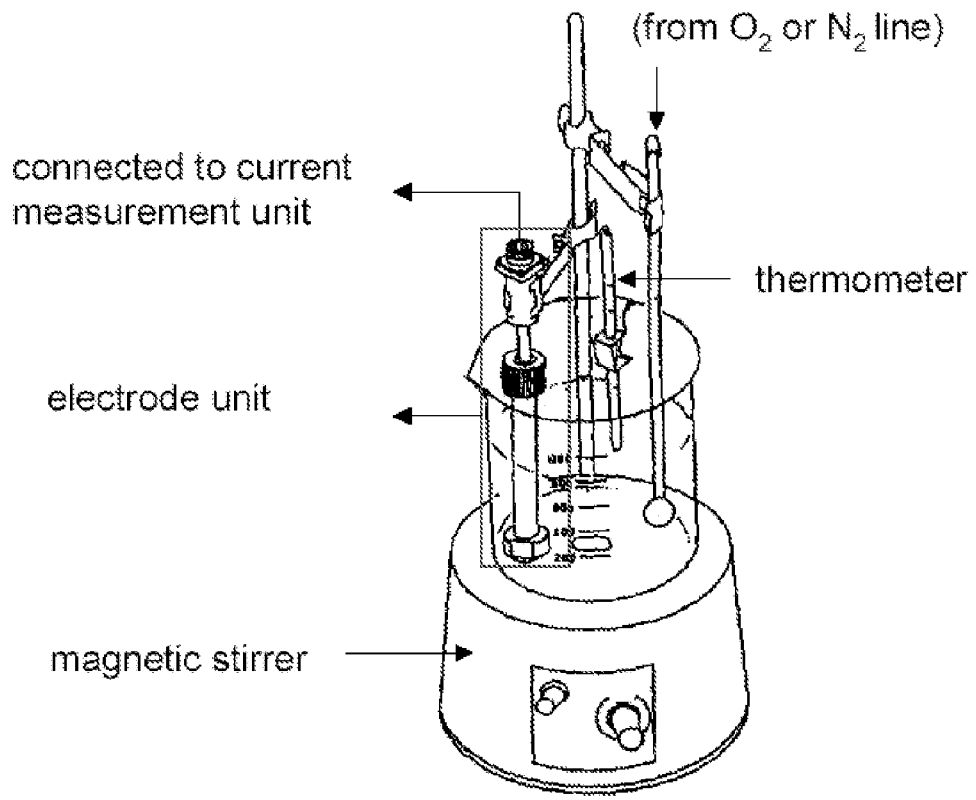
FIG. 2 shows an apparatus for oxygen permeability measurement.
Figure 3:
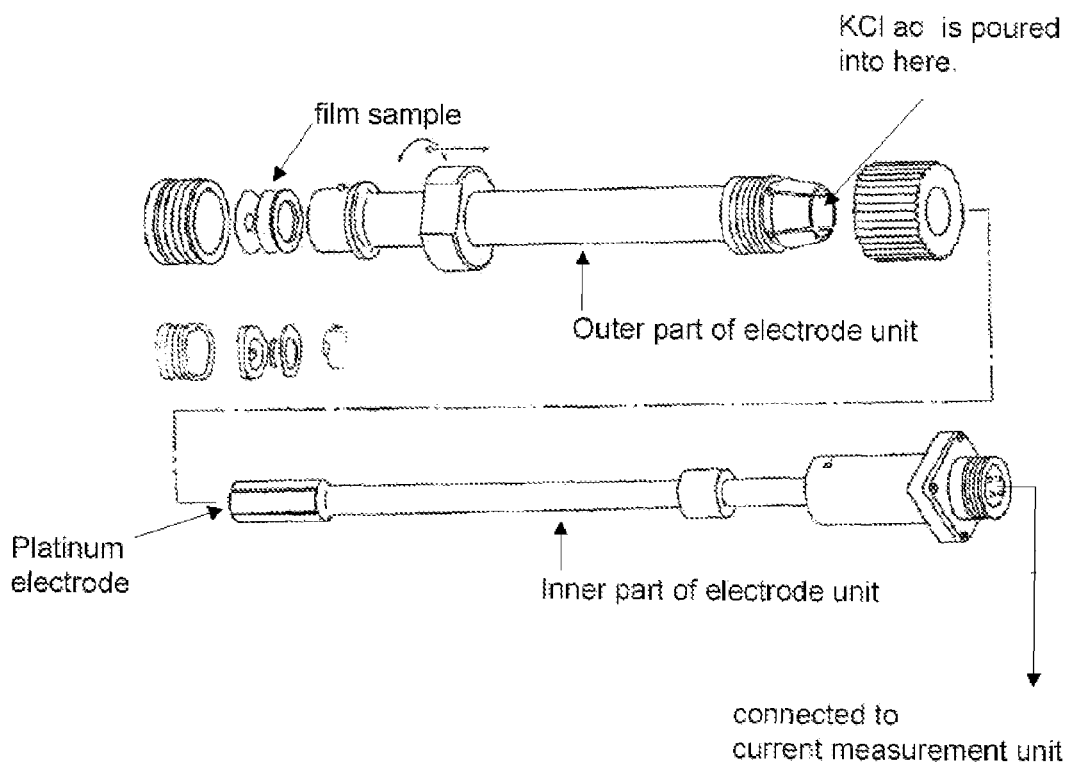
FIG. 3 shows the structure of an electrode unit used to measure oxygen permeability.
Figure 4:
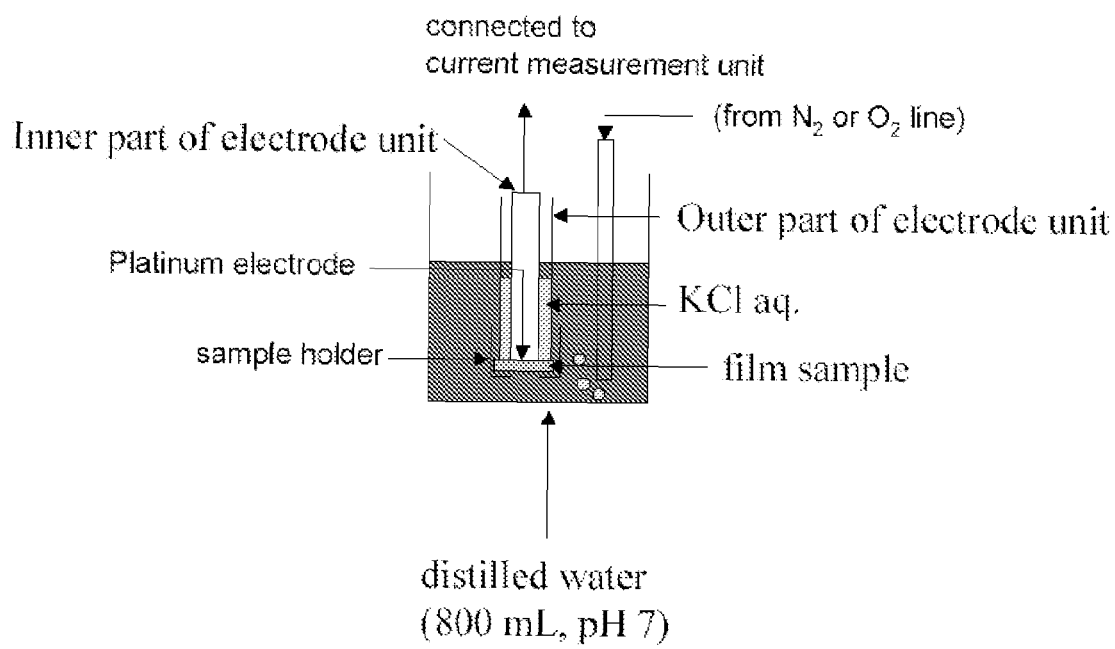
FIG. 4 shows a schematic of an oxygen permeability measurement setup.

A sample's oxygen permeability coefficient was determined by using a Seikaken-shiki film oxygen permeability meter manufactured by RIKA SEIKI KOGYO CO., LTD. The oxygen permeability coefficient of a sample in the form of a film was measured in water at 35° C. (temperature controller not shown in Figure). Stirring was performed at a rate of 800 rpm with a 3 mm octagon-type MAGMIX magnetic stirrer (Mitamura Riken Kogyo Inc.). Four film samples with different thickness were prepared (0.1 mm, 0.2 mm, 0.3 mm, and 0.4 mm; diameter 16 mm). The four samples with different thickness were measured to determine Pm of every example (see FIG. 1); the graduation of the dial upright gauge used was 0.001 mm; with an accuracy of about +/−0.003 mm. One of the samples was set on an electrode. 0.5 N KCl (aqueous) was poured into the electrode as an electrolytic solution (see FIGS. 2-4). The electrode was set in distilled water (pH=7, volume=800 ml). At first, the current under nitrogen bubbling (flow rate=100 mL/min.; electric current, i, is measured after it is in equilibrium) was measured in order to adjust zero. Then the current under oxygen bubbling was measured. R was calculated by the following formula: R=(Ps×N×F×A)/i [$cm^2$ sec mmHg/mL (STP)] (wherein Ps=760 mmHg (atmospheric pressure), N=4 (the number of electrons which involves a reaction at the electrode), F=96500 coulomb/mol (Faraday constant), A=area of the electrode ($cm^2$), i=measured current (uA)). R involves constant (not proportional) part, so plural measurement and plotting are necessary to determine Pm (see FIG. 1). R versus the thickness of the samples was plotted. The inverse of the slope is the oxygen permeability coefficient (Pm).

In oxygen permeability testing, edge correction is typically considered when the area of a material through which oxygen passes differs from one surface of the sample to the other surface. In the present measurement method, the area of the hole of the ring which is set next to a film sample (see FIG. 3, upper left portion) is the same as the area of platinum electrode, so edge correction is unnecessary.

Moisture Content: a sample in the form of a film sizing about 10 mm×10 mm×0.2 mm was used. The sample was dried in a vacuum dryer at 40° C. for 16 hours, and the weight (Wd) of the sample was measured. Thereafter, the resulting sample was immersed in pure water at 40° C. in a thermostat bath overnight or more, and the moisture on the surface was wiped with Kimwipe, followed by measurement of the weight (Ww). The moisture content was calculated according to the following equation:

$$\text{Moisture Content (\%)}=100\times(Ww-Wd)/Ww$$

Tensile Test: a sample in the form of a film sizing about 19.5 mm×15 mm×0.2 mm was used. The tensile modulus of elasticity was measured using Tensilon type RTM-100 manufactured by ORIENTEC. The speed of pulling was 100 mm/min and the distance between grips was 5 mm.

Optical Non-uniformity of Molded Plastics: a sample molded into the form of contact lens was irradiated with light with a projector for photograph films to project its image on a screen, and the projected image on the screen was visually observed to evaluate the degree of optical non-uniformity. The evaluation was performed by classification into the following three ranks:

A: Distortion or turbidity is not observed at all.

B: Distortion or turbidity is observed very slightly.

C: Distortion or turbidity is observed.

b. Reference Example 1

To a 1 L three-necked round bottom flask, methacrylic acid (241.2 g), allylglycidyl ether (80.3 g), sodium methacrylate (22.7 g) and 4-methoxyphenol (1.14 g) were added, and the mixture was stirred with a mechanical stirrer. The flask was immersed in an oil bath to raise the temperature to 100° C., and the mixture was stirred for 4 hours under heat while tracing the reaction by gas chromatography (GC) analysis. After allowing the mixture to cool, toluene (300 mL) was added, and the resulting mixture was transferred to a 1 L separatory funnel. The mixture was washed with 0.5N aqueous sodium hydroxide solution (300 mL) 7 times and then with saturated saline (300 mL) 3 times. The organic layer was collected and dried over anhydrous sodium sulfate overnight. After removing the solids by filtration, the filtrate was recovered in a 1 L eggplant type flask, and the solvent was evaporated. The resultant was then transferred to a 500 mL eggplant type flask, and 2,6-di-t-butyl-4-methylphenol (0.23 g) was added thereto, followed by further concentration of the resultant (yield: 226.74 g). To the resultant, aluminum N-nitrosophenylhydroxylamine (0.23 g) was added, followed by distillation under reduced pressure, thereby obtaining the material for producing molded plastics, characterized by containing the compound represented by Formula (F1-1) or Formula (F1-2) below.

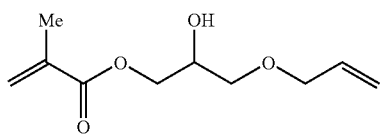

(F1-1)

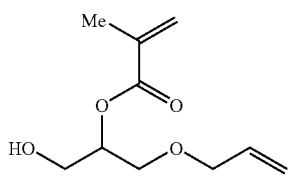

(F1-2)

c. Example 1

To a 200 mL three-necked round bottom flask to which a Dimroth condenser was connected, which Dimroth condenser is connected to a nitrogen line, the mixture (50 g) of the compound represented by Formula (F1-1) and the compound represented by Formula (F1-2) obtained in Reference Example 1, hexamethyldisilazane (24.34 g), 2,6-di-t-butyl-4-methylphenol (0.161 g) and saccharin (0.148 g) were added, and the resulting mixture was heated in an oil bath at 100° C. under stirring with a magnetic stirrer. Ammonia gas was generated during heating. Forty five minutes later heating and stirring were stopped and the mixture was allowed to cool to room temperature, followed by filtrating the reaction solution to remove the solids. To the resultant, 2,6-di-t-butyl-4-methylphenol (0.32 g) and aluminum N-nitrosophenylhydroxylamine (0.32 g) were added, followed by distillation under reduced pressure, thereby obtaining the material for producing molded plastics, characterized by containing the compound represented by Formula (F2-1) or Formula (F2-2) below. GC analysis revealed that the content of the compound was 97%.

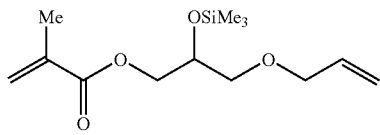

(F2-1)

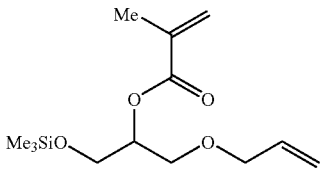

(F2-2)

d. Reference Example 2

To a 1 L three-necked round bottom flask, a 200 mL dropping funnel and a three way stopcock were connected, and the three way stopcock was connected to a vacuum pump and to a nitrogen line. The resulting apparatus was heated with a heat gun while reducing the pressure in the apparatus with the vacuum pump, and then nitrogen was blown thereinto to restore the pressure to the normal pressure. This operation was repeated three times to remove the moisture in the apparatus. To the flask, hexamethylcyclotrisiloxane (22.25 g, 0.1 mol) and toluene (25.7 mL) were added, and the resulting mixture was stirred with a magnetic stirrer. After the hexamethylcyclotrisiloxane was completely dissolved, the flask was immersed in a water bath (room temperature), and 169 mL (0.27 mol) of 1.6 mol/L butyl lithium solution in hexane was added dropwise to the mixture for 34 minutes, followed by stirring the resulting mixture for 1 hour at room temperature. The flask was cooled in a NaCl-containing ice bath, and a solution prepared by dissolving hexamethylcyclotrisiloxane (66.75 g, 0.3 mol) in anhydrous tetrahydrofuran (165 mL) was added dropwise for 60 minutes. The resulting mixture was stirred for 150 minutes under the cooled condition and then stirred at room temperature for 45 minutes. Dimethylchlorosilane (39 mL) was dissolved in tetrahydrofuran (100 mL) and the solution was added dropwise to the mixture for 45 minutes, followed by stirring the resulting mixture for 1 hour. The solution was washed with about 400 mL of water 4 times (with totally about 1.6 L of water), and the organic layer was dried over anhydrous sodium sulfate. After removing the solids by filtration through a pleated filter, the filtrate was recovered in an eggplant type flask, and the solvent was evaporated. The resultant was purified with a semi-micro rectification apparatus (SOGO LABORATORY GLASS WORKS CO., LTD., catalogue No. 2004) to obtain the compound represented by Formula (F3) below (GC purity: 99%).

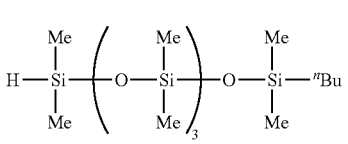

(F3)

e. Example 2

To a 200 mL eggplant type flask, the mixture (3.96 g) of the compound represented by Formula (F2-1) and the compound represented by Formula (F2-2) obtained in Example 1, toluene (4 mL), active carbon catalyst carrying 5% of platinum (WAKO PURE CHEMICAL, 308 mg) and a magnet bar were added, and a Dimroth condenser, to which a calcium chloride tube was connected at an upper portion thereof, was connected to the flask. The resulting mixture was heated to 80° C. under nitrogen atmosphere and under making the cooling water flow through the condenser. After the temperature of the mixture reached to 80° C., the compound (4.0 g) represented by Formula (F3) obtained in Reference Example 2 was slowly added dropwise to the mixture with a Pasteur pipette. After the reaction was completed, the mixture was filtered through Celite to remove the catalyst. Briefly, the reaction solution was filtered through Celite-535 together with hexane under reduced pressure using a Kiriyama funnel in which a filter paper was placed, the funnel being loaded with Celite-535 up to half the depth of the funnel. The filtrate was then concentrated with a rotatory evaporator (water bath: 40° C.). The concentrated reaction solution was transferred to a wide-necked, eggplant type flask (100 mL), and aluminum N-nitrosophenylhydroxylamine was added thereto as a polymerization inhibitor at a concentration of about 0.1 weight % of the reaction solution. Then a magnetic bar was added to the flask and the flask was fixed to a stand. The pressure in the flask was reduced with a vacuum pump at room temperature until substantially no bubbles were generated in the solution. After opening the upper valve fully, the reaction solution was heated to 140° C. by immersing the flask containing the reaction solution in an oil bath, and then low-boiling components were removed by aspiration with a vacuum pump under stirring the reaction solution for 1 hour, thereby obtaining the material for producing molded plastics, characterized by containing the compound represented by Formula (F4-1) or Formula (F4-2) below. GC analysis revealed that the content of the compound represented by Formula (F4-1) and the compound represented by Formula (F4-2) in all components of the obtained material (i.e., purity) was 96%. The number of the peaks observed in GC was 18, and there were very few impurities in the obtained material.

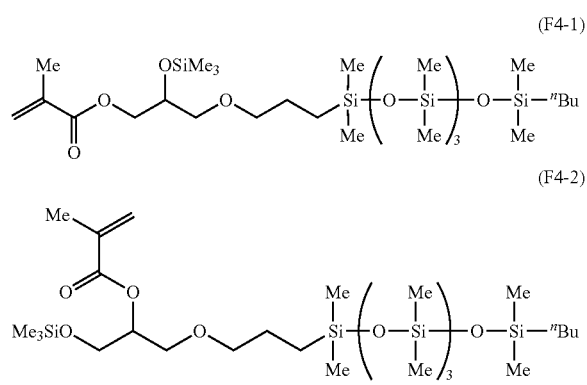

f. Example 3

The material (6.34 g) for producing molded plastics characterized by containing the compound represented by Formula (F4-1) or Formula (F4-2), methanol (19.02 g) and acetic acid (3.17 g) were mixed and shaken lightly to make the mixture homogeneous, followed by leaving the mixture to stand for 30 minutes at normal temperature. Thereafter, methanol was removed by using a rotatory evaporator.

To the concentrated solution (6.34 g), hexane (25.36 g) was mixed, and the mixture was washed using a separatory funnel with purified water (25.36 g) 3 times, then with the same amount of saturated sodium bicarbonate solution (25.36 g) twice, and finally with the same amount of purified water (25.36 g) 3 times. The hexane layer alone was collected into an Erlenmeyer flask, dried over anhydrous sodium sulfate, and concentrated with a rotatory evaporator.

Then 2.0 g aliquot of the product obtained by concentration was purified by silica gel column chromatography using silica gel (9 g) and using as a developing solvent a mixed solvent of hexane:ethyl acetate, thereby obtaining the material for producing molded plastics, characterized by containing the compound represented by Formula (F5-1) or Formula (F5-2) below. The yield from column chromatography was 68%. GC analysis revealed that the content of the compound represented by Formula (F5-1) and the compound represented by Formula (F5-2) in all components of the obtained material (i.e., purity) was 96%. The number of the peaks observed in GC was 15, and there were very few impurities in the obtained material.

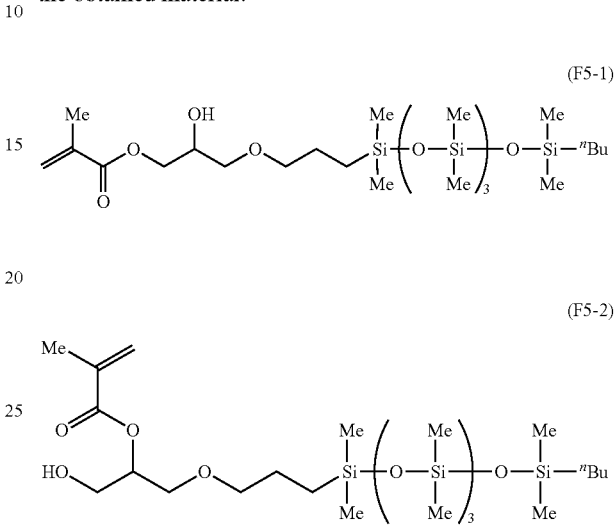

g. Reference Example 3

To a 1 L three-necked round bottom flask, a 200 mL dropping funnel and a three way stopcock were connected, and the three way stopcock was connected to a vacuum pump and to a nitrogen line. The resulting apparatus was heated with a heat gun while reducing the pressure in the apparatus with the vacuum pump, and then nitrogen was blown thereinto to restore the pressure to the normal pressure. This operation was repeated three times to remove the moisture in the apparatus. To the flask, hexamethylcyclotrisiloxane (22.25 g, 0.1 mol) and toluene (25.7 mL) were added, and the resulting mixture was stirred with a magnetic stirrer. After the hexamethylcyclotrisiloxane was completely dissolved, the flask was immersed in a water bath (room temperature), and 169 mL (0.27 mol) of 1.6 mol/L butyl lithium solution in hexane was added dropwise to the mixture for 35 minutes, followed by stirring the resulting mixture for 1 hour at room temperature. The flask was cooled in an NaCl-containing ice bath, and a solution prepared by dissolving hexamethylcyclotrisiloxane (133.5 g, 0.6 mol) in anhydrous tetrahydrofuran (165 mL) was added dropwise for 60 minutes. The resulting mixture was stirred for 150 minutes under the cooled condition and then stirred at room temperature for 45 minutes. Dimethylchlorosilane (39 mL) was dissolved in tetrahydrofuran (100 mL) and the solution was added dropwise to the mixture for 45 minutes, followed by stirring the resulting mixture for 1 hour. The solution was washed with about 400 mL of water 4 times (with totally about 1.6 L of water), and the organic layer was dried over anhydrous sodium sulfate. After removing the solids by filtration through a pleated filter, the filtrate was recovered in an eggplant type flask, and the solvent was evaporated. The resultant was purified with a semi-micro rectification apparatus (SOGO LABORATORY GLASS WORKS CO., LTD., catalogue No. 2004) to obtain the compound represented by Formula (F6) below (GC purity: 98%).

(F6)
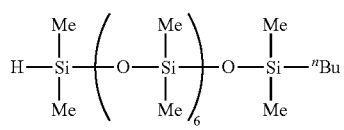

h. Example 4

The same procedure as in Example 2 was carried out except that the compound represented by Formula (F6) (5.7 g) obtained in Reference Example 3 was used in place of the compound represented by Formula (F3) (4.0 g) to obtain the material for producing molded plastics characterized by containing the compound represented by Formula (F7-1) or Formula (F7-2) below. GC analysis revealed that the content of the compound represented by Formula (F7-1) and the compound represented by Formula (F7-2) in all components of the obtained material (i.e., purity) was 95%. The number of the peaks observed in GC was 19, and there were very few impurities in the obtained material.

(F7-1)

(F7-2)

i. Example 5

The same procedure as in Example 3 was carried out except that the material (6.34 g) for producing molded plastics characterized by containing the compound represented by Formula (F7-1) or Formula (F7-2) obtained in Example 4 was used in place of the material (6.34 g) for producing molded plastics characterized by containing the compound represented by Formula (F4-1) or Formula (F4-2) to obtain the material for producing molded plastics characterized by containing the compound represented by Formula (F8-1) or Formula (F8-2) below. The yield from column chromatography was 70%. GC analysis revealed that the content of the compound represented by Formula (F8-1) and the compound represented by Formula (F8-2) in all components of the obtained material (i.e., purity) was 95%. The number of the peaks observed in GC was 16, and there were very few impurities in the obtained material.

(F8-1)
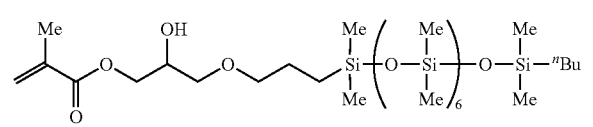

(F8-2)
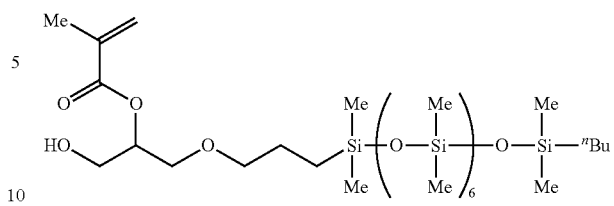

j. Reference Example 4

To a 200 mL three-necked round bottom flask to which a Dimroth condenser and a dropping funnel were connected, allylglycidyl ether (8.47 g), active carbon catalyst carrying 5% of platinum (WAKO PURE CHEMICAL, 153 mg) and toluene (20 mL) were added, and the mixture was heated in an oil bath at 80° C. under nitrogen atmosphere. The compound represented by the above-mentioned Formula (F3) (20 g) was added dropwise to the mixture. The reaction solution was stirred with magnetic stirrer for 90 minutes under heat. After allowing the mixture to cool, the mixture was filtered through a membrane filter (1 μm) with pressure to remove the catalyst. The solvent in the filtrate was evaporated, and the resultant was transferred to a 50 mL eggplant type flask. The resulting mixture was heated at 60° C. under stirring and under aspiration with the vacuum pump to remove low-boiling components, thereby obtaining the compound represented by Formula (F9) below. GC analysis revealed that the purity of the compound was 97.5%.

(F9)

k. Comparative Example 1

To a 50 mL three-necked round bottom flask to which a thermometer and a Dimroth condenser were connected, the compound represented by Formula (F9) (6.57 g) obtained in Reference Example 4, sodium methacrylate (0.81 g), methacrylic acid (8.58 g), 4-methoxyphenol (0.0207 g) and water (0.09 g) were added, and the flask was immersed in an oil bath at 100° C., followed by stirring the mixture for 4 hours. Hexane (15 mL) was added to the reaction solution, and the resultant was washed with 1N aqueous sodium hydroxide (30 mL) 3 times. The organic layer was collected and then washed with 2.45 weight % saline (30 mL) 3 times. To the organic layer, 4-t-butylcatechol (5 mg) was added, and the organic layer was dried over anhydrous sodium sulfate.

After removing the solids by filtration, the filtrate was evaporated. Then a 2.0 g aliquot of the product obtained by concentration was purified by silica gel column chromatography using silica gel (9 g) and using as a developing solvent a mixed solvent of hexane:ethyl acetate, thereby obtaining the material for producing molded plastics characterized by containing the compound represented by Formula (F5-1) or Formula (F5-2) below. The yield from column chromatography was 69%. GC analysis revealed that the content of the compound represented by Formula (F5-1) and the compound represented by Formula (F5-2) in all components of the obtained material (i.e., purity) was 95%. The number of the peaks observed in GC was 35, and there were a great many impurities in the obtained material.

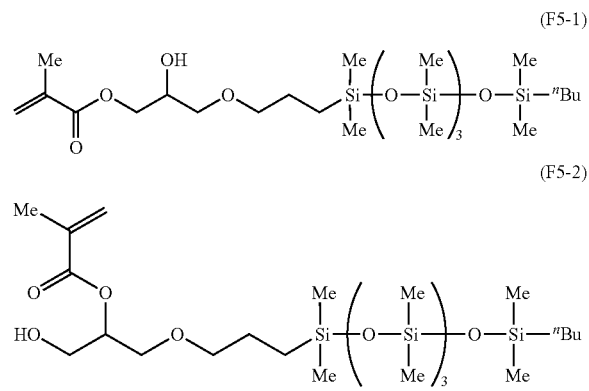

(F5-1)

(F5-2)

l. Example 6

The material (1 g) for producing molded plastics characterized by containing the compound represented by Formula (F2-1) or Formula (F2-2) obtained in Example 1 (hereinafter referred to as "material F2") and the compound represented by Formula (F10) below (average molecular weight: 1000, 1 g) were mixed to be a homogeneous and clear mixture, indicating that the material F2 had good compatibility with a siloxanyl monomer.

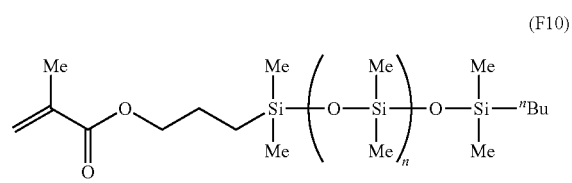

(F10)

m. Comparative Example 2

The material (1 g) for producing molded plastics characterized by containing the compound represented by Formula (F1-1) or Formula (F1-2) obtained in Reference Example 1 (hereinafter referred to as "material F1") and the compound represented by the above-mentioned Formula (F10) (average molecular weight: 1000, 1.0 g) were mixed. As a result, phase separation occurred. Thus, the material F1 was poor in compatibility with the siloxanyl monomer.

n. Comparative Example 3

2-Hydroxyethyl methacrylate (1 g) and the compound represented by the above-mentioned Formula (F10) (average molecular weight: 1000, 1 g) were mixed. As a result, phase separation occurred. Thus, 2-hydroxyethyl methacrylate was poor in compatibility with the siloxanyl monomer.

For the following examples, GC was carried out under the following conditions: Apparatus and Parameters: Apparatus: Model GC6890 manufactured by HEWLETT-PACKARD or equivalent thereof. Detector: hydrogen flame ionization detector (FID). Column: Agilent Technologies/J&W Scientific Ultra-2 (25 m×0.32 mm I.D.). Carrier Gas: helium. Constant Pressure: 110 kPa. Amount of Applied Sample: 2.0 μL. Split Ratio: 50:1. Inlet Temperature: 325° C. Detector Temperature: 350° C. Solvent for Washing Autosampler: 2-propanol. Inlet Septum: Alltech 7/16" HT-X-11 or equivalent. Temperature Program: Initial Temperature: 100° C. Initial time: 1 min. Ramp: 10° C./min; Final Temp: 320° C.; hold for 17 min. Sample Preparation: about 50 μL of a sample is dissolved in 1.0 mL of 2-propanol. The sample and 2-propanol are directly placed in a vial for GC and mixed therein. Calculation of Purity: Purity was calculated from the peak area of GC chromatogram.

o. Example 11

To a 50 mL eggplant type flask, 0.5 g (3.0 mmol) of a mixture of the compounds represented by the above-described Formula (F1-1) and Formula (F1-2), 19.6 mg of 5% Pt/C catalyst and 1 mL of toluene were added, and the flask was immersed in an oil bath while stirring the mixture under nitrogen atmosphere. After raising the temperature of the oil bath to 60° C., 1.03 g (2.5 mmol) of the compound represented by the above-described Formula (F3) was added dropwise, and the resulting mixture was stirred under heat for 60 minutes to obtain the desired mixture of the siloxanyl monomers represented by Formula (F4-1) and Formula (F4-2) below. After completion of the reaction, the purity of the desired product was measured by gas chromatography (GC). In cases where the starting material(s) remained, the GC purity of the desired product was calculated by excluding the peak area(s) of the starting material(s).

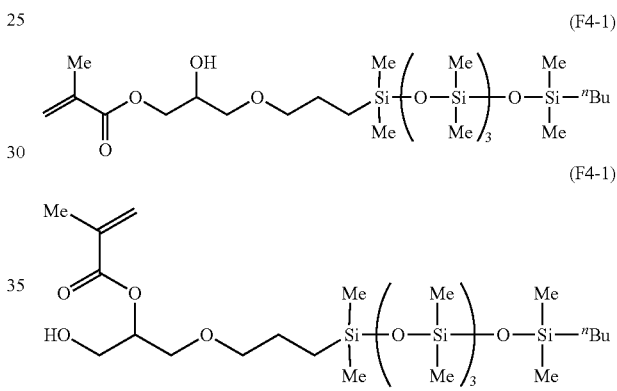

(F4-1)

(F4-1)

p. Examples 12 to 20 and 31-35

The same procedures as in Example 11 were repeated except that the mixture of the compounds represented by the above-described Formula (F1-1) and (F1-2) was used in an amount shown in Table 1, and the reaction atmosphere was changed to that shown in Table 1. The GC purities of the desired products are shown in Table 1. In Table 1, X represents the number of moles of the mixture of the above-described Formula (F1-1) and (F1-2) used, and Y represents the number of moles of the compound represented by the above-described Formula (F3) used.

TABLE 1

| | reaction atmosphere | X (m mol) | Y (m mol) | X/Y | purity (%) |
|---|---|---|---|---|---|
| Example 11 | $N_2$ | 3 | 2.5 | 1.2 | 87.8 |
| Example 12 | $N_2$ | 3.75 | 2.5 | 1.5 | 90.5 |
| Example 13 | $N_2$ | 5 | 2.5 | 2.0 | 93.7 |
| Example 14 | $N_2$ | 6.25 | 2.5 | 2.5 | 94.8 |
| Example 15 | $N_2$ | 7.5 | 2.5 | 3.0 | 95.7 |
| Example 16 | $N_2$ | 10 | 2.5 | 4.0 | 89.1 |
| Example 17 | $N_2$ | 12.5 | 2.5 | 5.0 | 91.7 |
| Example 18 | $N_2$ | 25 | 2.5 | 10.0 | 88.1 |
| Example 19 | air | 7.5 | 2.5 | 3.0 | 93.3 |
| Example 20 | $N_2$ | 2.875 | 2.5 | 1.15 | 82.2 |
| Example 31 | $N_2$ | 2.5 | 2.5 | 1.0 | 71.9 |
| Example 32 | $N_2$ | 2.75 | 2.5 | 1.1 | 73.6 |

TABLE 1-continued

|  | reaction atmosphere | X (m mol) | Y (m mol) | X/Y | purity (%) |
|---|---|---|---|---|---|
| Example 33 | N$_2$ | 50 | 2.5 | 20.0 | 79.8 |
| Example 34 | air | 2.75 | 2.5 | 1.1 | 70.6 |
| Example 35 | air | 37.5 | 2.5 | 15.0 | 81.1 | q. Examples 21 to 27 and 36 to 39

The same procedures as in Example 11 were repeated except that a mixture of the compounds represented by the above-described Formula (F2-1) and (F2-2) was used in an amount shown in Table 2, in place of the mixture of the compounds of the above-described Formula (F1-1) and (F1-2), and the reaction temperature was changed to 80° C. to obtain a desired mixture of the siloxanyl compounds represented by Formula (F5-1) and (F5-2) below. After completion of the reaction, the purity of the desired product was measured by gas chromatography (GC). In cases where the starting material(s) remained, the GC purity of the desired product was calculated by excluding the peak area(s) of the starting material(s).

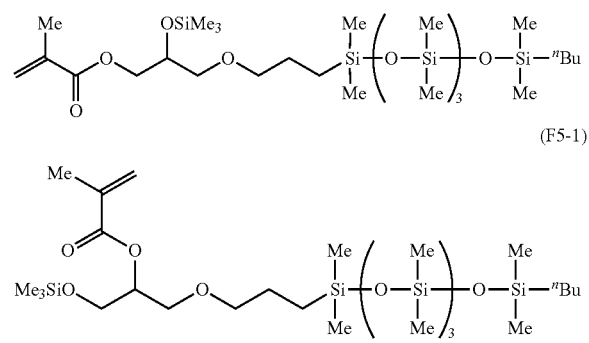

The GC purities of the desired products are shown in Table 2. In Table 2, X represents the number of moles of the mixture of the above-described Formula (F2-1) and (F2-2) used, and Y represents the number of moles of the compound represented by the above-described Formula (F3) used.

TABLE 2

|  | X (mmol) | Y (mmol) | X/Y | purity (%) |
|---|---|---|---|---|
| Example 21 | 7.5 | 2.5 | 3.0 | 85.1 |
| Example 22 | 6.25 | 2.5 | 2.5 | 87.0 |
| Example 23 | 5 | 2.5 | 2.0 | 87.7 |
| Example 24 | 3.75 | 2.5 | 1.5 | 88.1 |
| Example 25 | 3.5 | 2.5 | 1.4 | 90.6 |
| Example 26 | 3.25 | 2.5 | 1.3 | 86.8 |
| Example 27 | 3 | 2.5 | 1.2 | 87.8 |
| Example 36 | 30 | 2.5 | 12.0 | 79.8 |
| Example 37 | 2.75 | 2.5 | 1.1 | 73.6 |
| Example 38 | 2.5 | 2.5 | 1.0 | 71.9 |
| Example 39 | 2 | 2.5 | 0.8 | 81.3 | r. Reference Example 7

To a three-necked 1000 mL round bottom type flask, the mixture (0.5 mol) of the compound represented by Formula (F1-1) and the compound represented by Formula (F1-2) obtained in Reference Example 1, toluene (103 mL), active carbon catalyst carrying 5% of platinum (WAKO PURE CHEMICAL, 196 mg) and a magnet bar were added, and a Dimroth condenser, to which a calcium chloride tube was connected at an upper portion thereof, was connected to the flask. The resulting mixture was heated to 60° C. under nitrogen atmosphere and under making the cooling water flow through the condenser. After the temperature of the mixture reached to 60° C., the compound (0.25 mol) represented by Formula (F3) obtained in Reference Example 3 was slowly added dropwise to the mixture with a dropping funnel. After the reaction was completed, the mixture was filtered through Celite to remove the catalyst. Briefly, the reaction solution was filtered through Celite-535 together with hexane under reduced pressure using a Kiriyama funnel in which a filter paper was placed, the funnel being loaded with Celite-535 up to half the depth of the funnel. The filtrate was then concentrated with a rotatory evaporator (water bath: 40° C.), thereby obtaining the siloxanyl monomer, characterized by containing the compound represented by Formula (F4-1) or Formula (F4-2).

s. Example 28

To 200 g of the siloxanyl monomer (crude product) obtained in Reference Example 7, 2,6-di-t-butyl-4-methylphenol (0.4 g) was added and dissolved. Using a thin film distillation apparatus (short path distillation apparatus) type KDL5 manufactured by UIC GmbH, thin film distillation was carried out under the following conditions to separate the solution to distillate and non-distillate (residual solution).

GC analysis of the non-distillate (residual solution) was carried out. As a result, the amount of the compounds represented by the above-described Formula (F1-1) and Formula (F1-2) was less than 0.1%. The recovery of the residual solution was 92% based on the theoretical value. By the GPC analysis, polymerized products were not detected.

Conditions of the thin film distillation: Distillation Temperature: 100° C.; Inner Condenser Temperature: 40° C.; Inner Pressure: full vacuum (0.02 mbar or less, the value indicated by the vacuum meter appended to the apparatus); Wiper Speed: 350 rpm; Feed Rate: 80 g/h.

t. Example 40

To a 300 mL eggplant type flask, 100 g of the siloxanyl monomer (crude product) obtained in Reference Example 7 was placed and 2,6-di-t-butyl-4-methylphenol (0.2 g) as a polymerization inhibitor was added thereto and dissolved. After placing a rotator in the flask, the flask was fixed to a stand and connected to a vacuum line equipped with a liquid nitrogen trap. The flask was aspirated with a vacuum pump at room temperature until bubbles were not substantially formed any more. The eggplant type flask containing the solution was immersed in an oil bath while keeping the connection with the vacuum line, and the temperature was raised to 140° C. From the time point at which the temperature reached 140° C., the mixture was stirred for 1 hour while continuing the aspiration by the vacuum pump to remove low boiling compounds. Since a prominent increase in the viscosity of the solution in the flask was observed, it was determined that polymerization occurred.

u. Example 29

To 187 g of the siloxanyl monomer (crude product) obtained in Reference Example 7, hexane (281 mL) was added and uniformly dissolved. Methanol (140 mL) and 3 wt % saline (140 mL) were added thereto, and the resulting mixture was transferred to a separation funnel, followed by vigorous shaking of the mixture. The mixture was then left to stand and the hexane layer was recovered. Again, methanol (140 mL) and 3 wt % saline (140 mL) were added, and the hexane layer was recovered by the same operation. This extraction operation was repeated a total of 6 times. The solvent was removed with a rotary vacuum evaporator. GC analysis of the obtained siloxanyl monomer revealed that the residual ratio of the compounds represented by the above-described Formula (F1-1) and Formula (F1-2) was 0.92%. The recovery rate of the siloxanyl monomer based on the theoretical value was 96%. By the GPC analysis, polymerized products were not detected.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for producing a siloxanyl monomer composition, the composition comprising monomers having the structures:

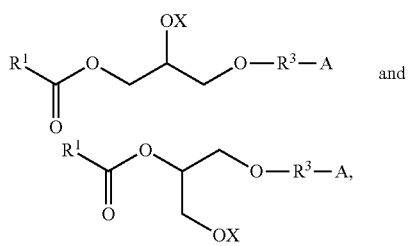

and wherein $R^1$ represents a $C_1$-$C_{20}$ substituent having at least one unsaturated bond,
wherein $R^3$ represents a $C_1$-$C_7$ divalent substituent,
wherein A represents a siloxanyl group, and
wherein X represents a hydrogen;
the method comprising the step of reacting unsaturated compounds having the structures:

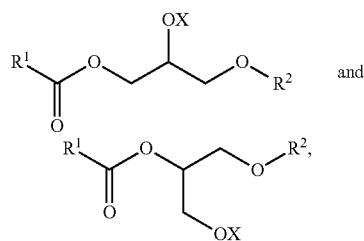

and wherein $R^1$ represents a $C_1$-$C_{20}$ substituent having at least one unsaturated bond,
wherein $R^2$ represents a $C_1$-$C_7$ substituent having at least one unsaturated bond, and
wherein X represents a hydrogen;
with a siloxanyl compound having a structure A-H, wherein A represents a siloxanyl group, in the presence of a metal catalyst,
thereby producing a reaction mixture containing a siloxanyl monomer;
wherein the molar ratio of the unsaturated compound to the siloxanyl compound is from about 1.2:1 to about 10:1 during the reacting step.

2. The method of claim 1, wherein the molar ratio of the unsaturated compounds to the siloxanyl compound is from about 2.5:1 to about 3:1 during the reacting step.

3. The method of claim 2, further comprising the sequential steps of:
a) mixing the reaction mixture with a hydrocarbon solvent and water and/or a $C_1$-$C_5$ alcohol;
b) allowing the mixture to form two layers; and
c) separating the two layers,
thereby removing the unsaturated compounds from the reaction mixture.

4. The method of claim 2, wherein the unsaturated compounds are removed from the reaction mixture by thin film distillation.

5. The method of claim 2, wherein the unsaturated compounds have the structures:

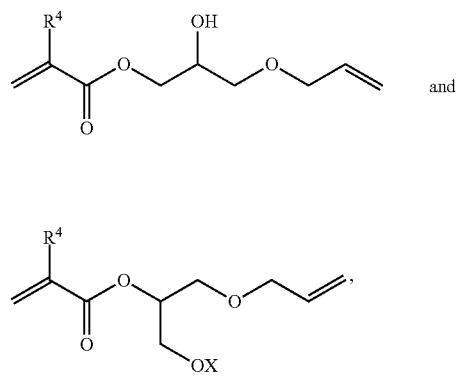

wherein $R^4$ is a hydrogen or a substituent selected from $C_1$-$C_{18}$ alkyl and phenyl; and
wherein X represents a hydrogen; and
wherein the siloxanyl monomer composition comprises monomers having the structures:

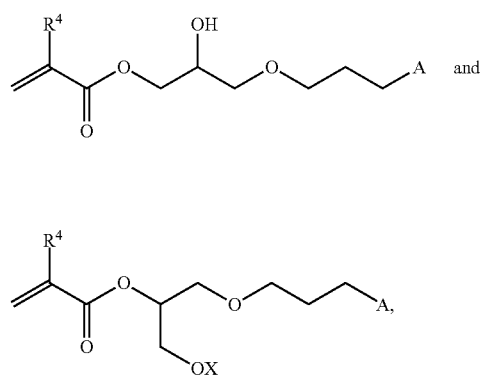

wherein $R^4$ is a hydrogen or a substituent selected from $C_1$-$C_{18}$ alkyl and phenyl;
wherein A is a siloxanyl group; and
wherein X represents a hydrogen.

6. The method of claim 2, wherein the siloxanyl compound has a structure:

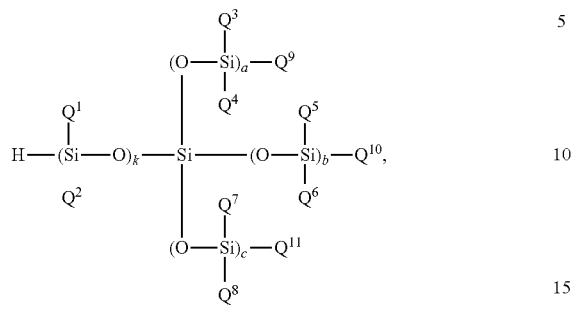

wherein $Q^1$ to $Q^{11}$ independently represent hydrogen or a substituent selected from $C_1$-$C_{20}$ alkyl which is optionally substituted and $C_6$-$C_{20}$ aryl which is optionally substituted;

wherein k represents an integer of 0 to 200; and wherein a, b, and c independently represent integers of 0 to 20, with the proviso that k, a, b, and c are not simultaneously zero.

* * * * *